(12) United States Patent
Sawada et al.

(10) Patent No.: US 7,692,364 B2
(45) Date of Patent: Apr. 6, 2010

(54) ULTRASONIC PROBE

(75) Inventors: Yukihiko Sawada, Yoshikawa (JP);
Akiko Mizunuma, Tokyo (JP);
Katsuhiro Wakabayashi, Tokyo (JP);
Takuya Imahashi, Kawasaki (JP);
Sunao Sato, Tokyo (JP)

(73) Assignees: Olympus Medical Systems Corporation, Tokyo (JP); Olympus Corporation, Tokyo (JP)

( * ) Notice: Subject to any disclaimer, the term of this patent is extended or adjusted under 35 U.S.C. 154(b) by 403 days.

(21) Appl. No.: 11/662,791

(22) PCT Filed: Sep. 13, 2005

(86) PCT No.: PCT/JP2005/016855

§ 371 (c)(1),
(2), (4) Date: Mar. 14, 2007

(87) PCT Pub. No.: WO2006/030793

PCT Pub. Date: Mar. 23, 2006

(65) Prior Publication Data

US 2007/0287920 A1    Dec. 13, 2007

(30) Foreign Application Priority Data

Sep. 16, 2004  (JP)  ............... 2004-270380
Jan. 28, 2005  (JP)  ............... 2005-022261
Feb. 1, 2005  (JP)  ............... 2005-025301

(51) Int. Cl.
*A61B 8/00* (2006.01)

(52) U.S. Cl. .............. 310/334; 310/311; 600/437; 600/439

(58) Field of Classification Search ........ 310/334; 604/96.01; 248/225.1
See application file for complete search history.

(56) References Cited

U.S. PATENT DOCUMENTS 5,342,126 A  *  8/1994  Heston et al. ............ 374/208

(Continued)

FOREIGN PATENT DOCUMENTS

JP    63-14623    3/1988

(Continued)

OTHER PUBLICATIONS

Electronic Industries Association of Japan, (currently, Japan Electronics and Information Technology Industries Association) : Handbook of Ultrasonic Diagnostic Equipments, pp. 114, published by Corona Publishing Co., Ltd.; dated Jan. 20, 1997.

*Primary Examiner*—Walter Benson
*Assistant Examiner*—Bryan P Gordon
(74) *Attorney, Agent, or Firm*—Scully, Scott, Murphy & Presser, P.C.

(57) ABSTRACT

An electronic radial ultrasonic probe comprising an electronic radial array which comprises a plurality of ultrasonic transducers being continuously arrayed circularly around an insertion axis as center and also for which a transmission/reception of an ultrasonic wave is controlled by electronically selecting the plurality of ultrasonic transducer, comprises: a support member equipped on the electronic radial array; a lock member featured with a cavity in which the support member is inserted and with a lock groove for locking a balloon which is mounted in a manner to cover the electronic radial array and in which an ultrasonic medium is filled; and a filler member which is constituted by an adhesive material converting from a fluid state to a solid state, and is filled in the cavity.

17 Claims, 42 Drawing Sheets

U.S. PATENT DOCUMENTS

| | | | |
|---|---|---|---|
| 6,142,945 A * | 11/2000 | Sakamoto et al. | 600/459 |
| 6,248,074 B1 * | 6/2001 | Ohno et al. | 600/463 |
| 6,796,960 B2 * | 9/2004 | Cioanta et al. | 604/103.01 |
| 2004/0049111 A1 * | 3/2004 | Hirooka et al. | 600/437 |
| 2004/0147939 A1 * | 7/2004 | Rabkin et al. | 606/108 |
| 2005/0256402 A1 * | 11/2005 | Kawashima et al. | 600/437 |

FOREIGN PATENT DOCUMENTS

| | | |
|---|---|---|
| JP | 6-13034 | 2/1994 |
| JP | 07-227393 | 8/1995 |
| JP | 08-215136 | 8/1996 |
| JP | 11-276486 | 10/1999 |
| JP | 2004-248990 | 9/2004 |

* cited by examiner

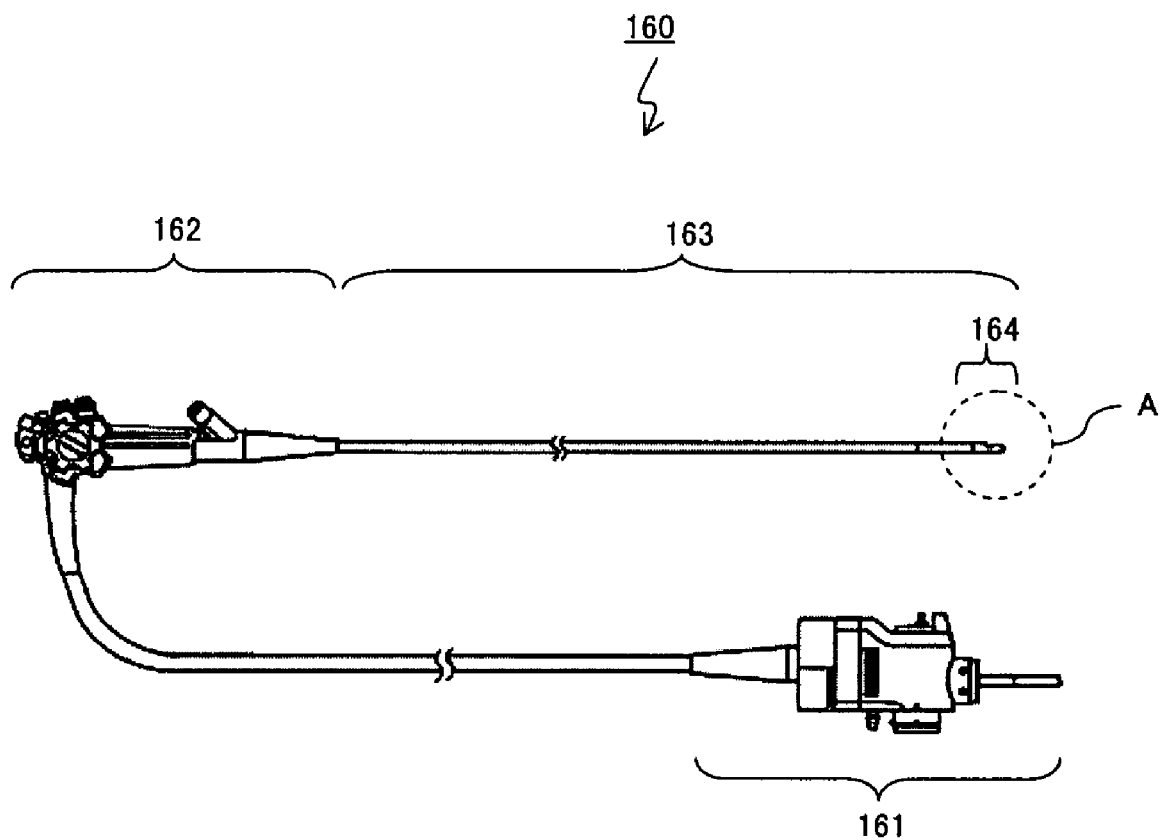
F I G. 1

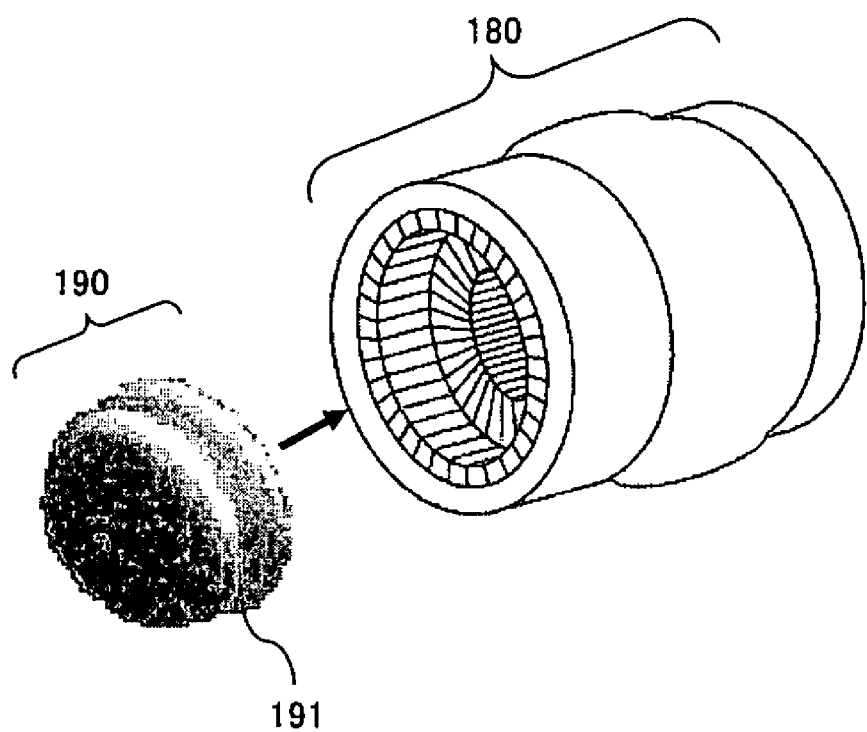
F I G. 4

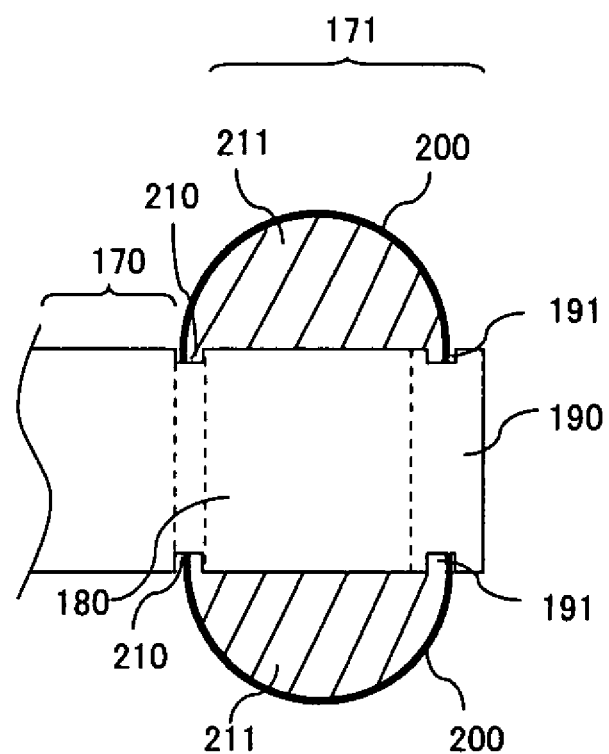
F I G. 6

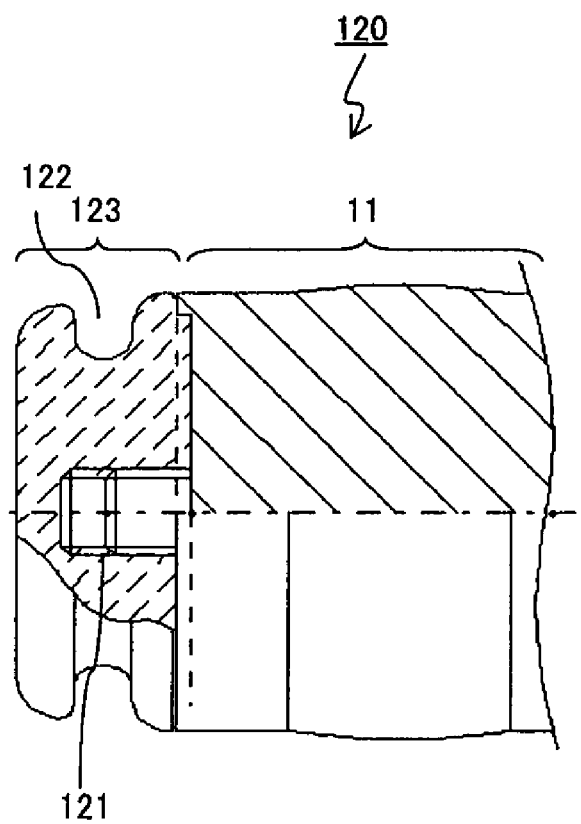
F I G. 21

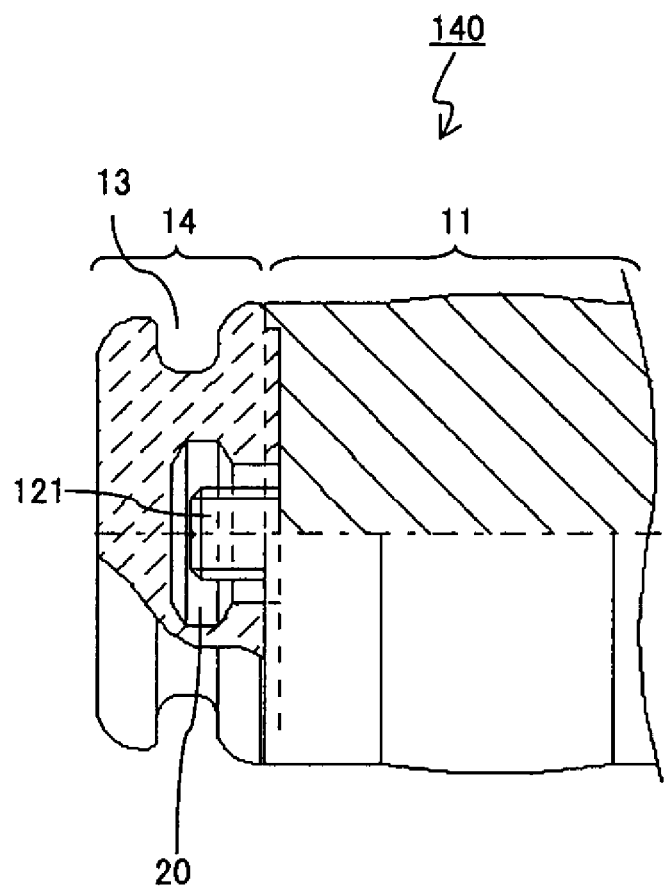
F I G. 2 3

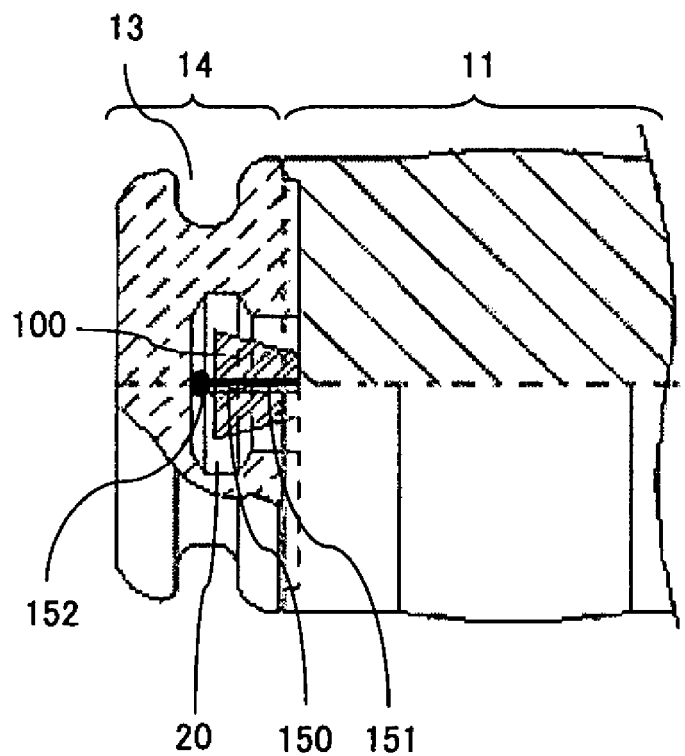
F I G. 24

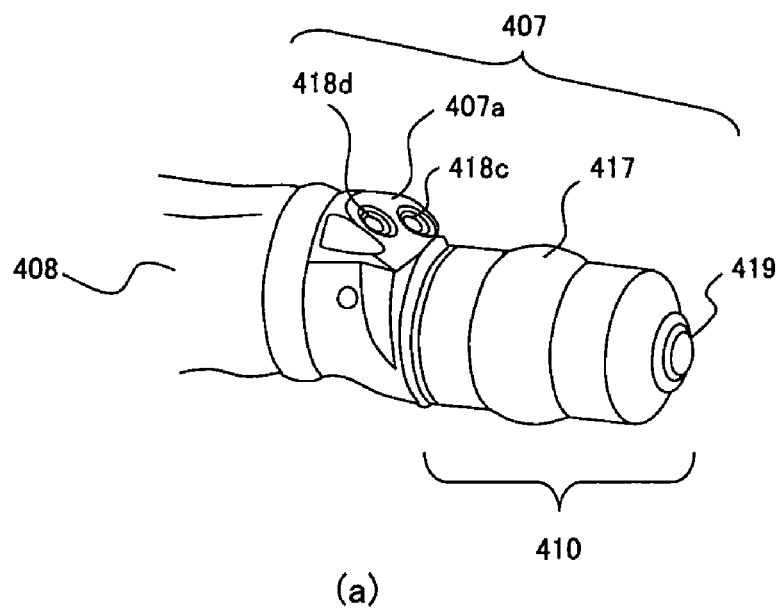
(a)
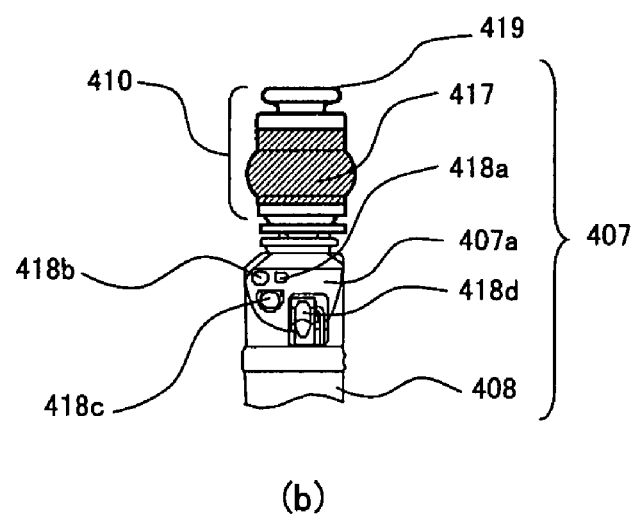
(b)
FIG. 30

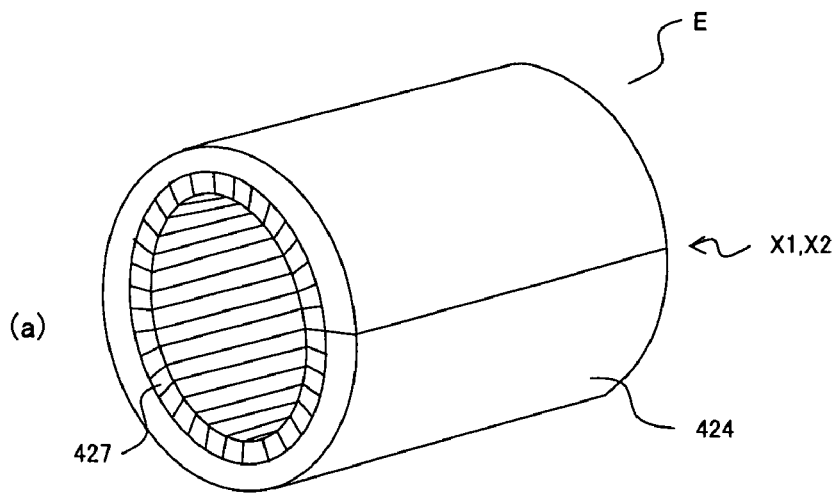
(a)
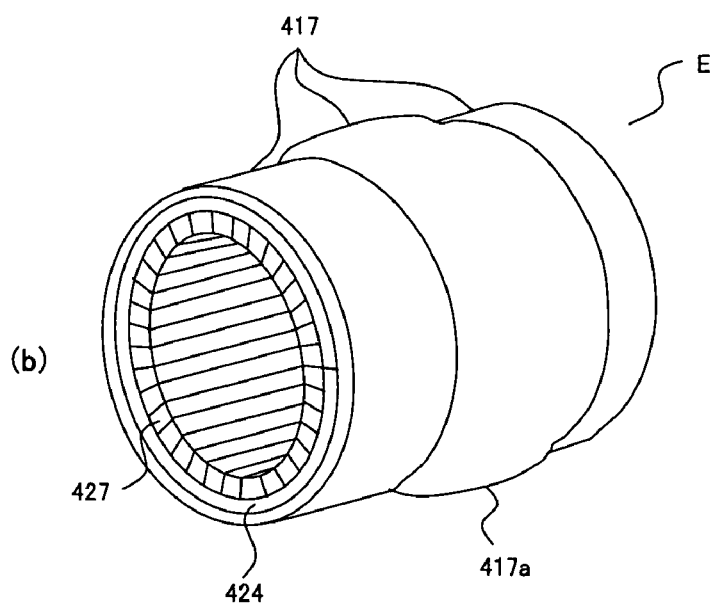
(b)
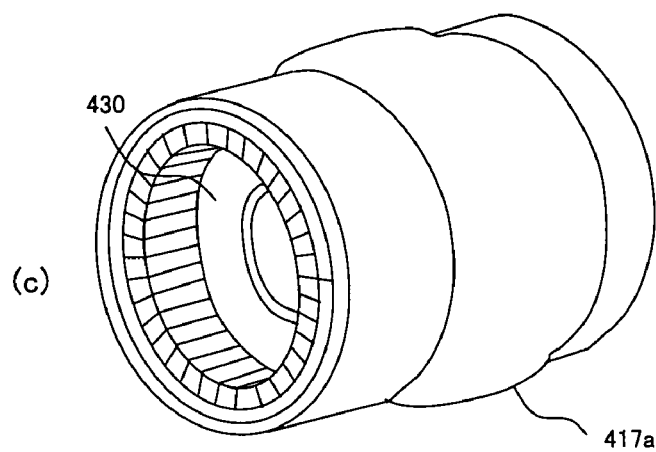
(c)
F I G. 3 2

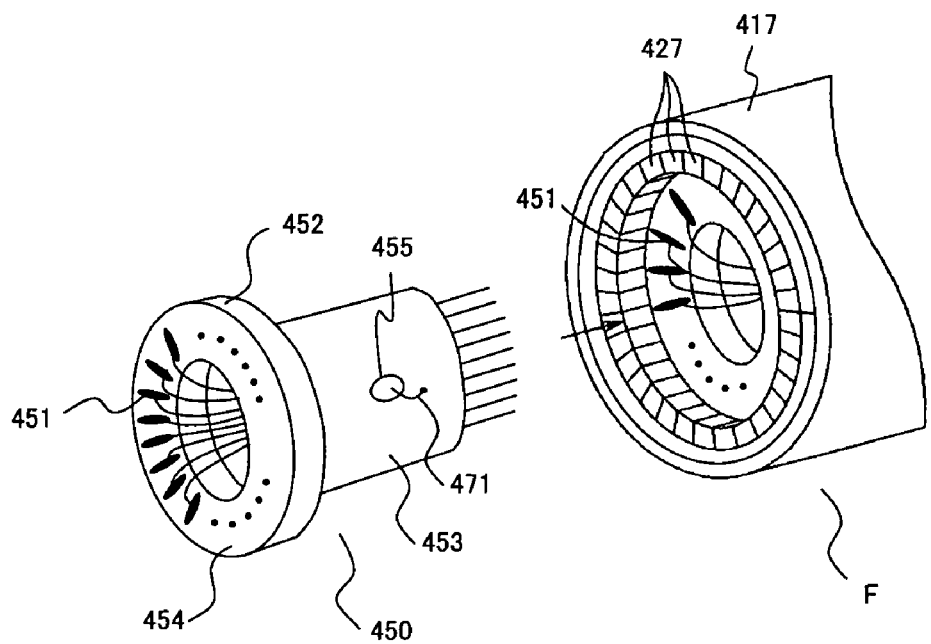
(a)
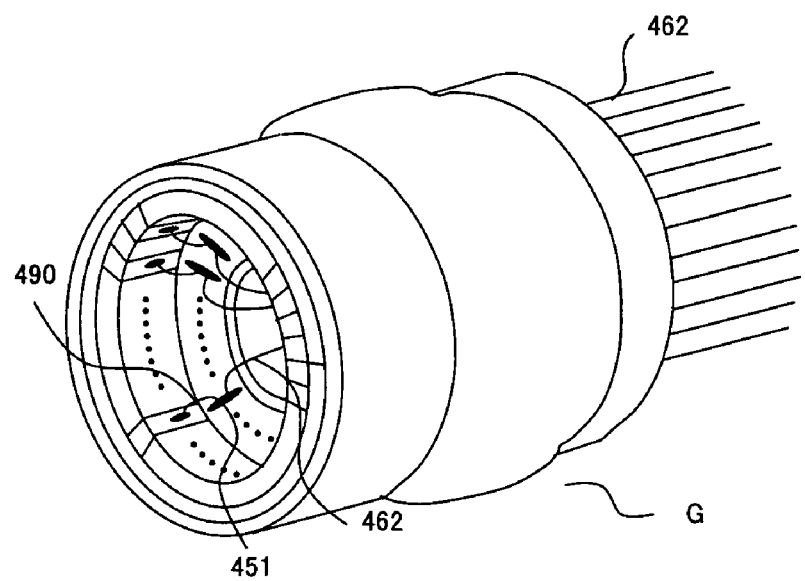
(b)
FIG. 34

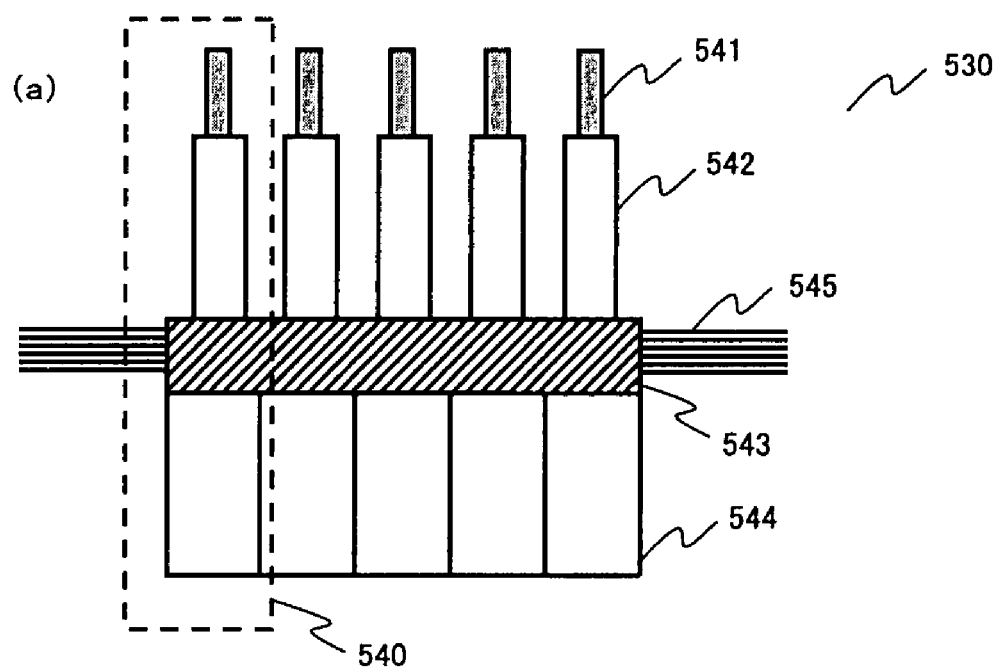
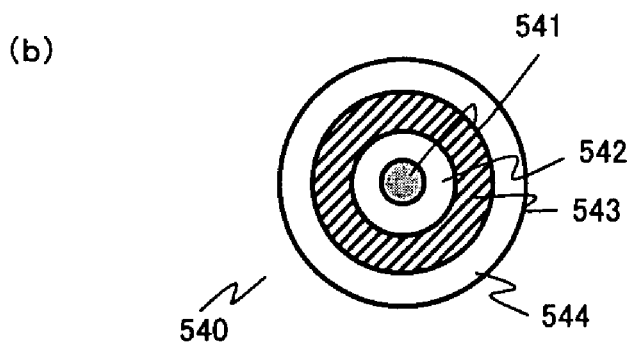
F I G. 38

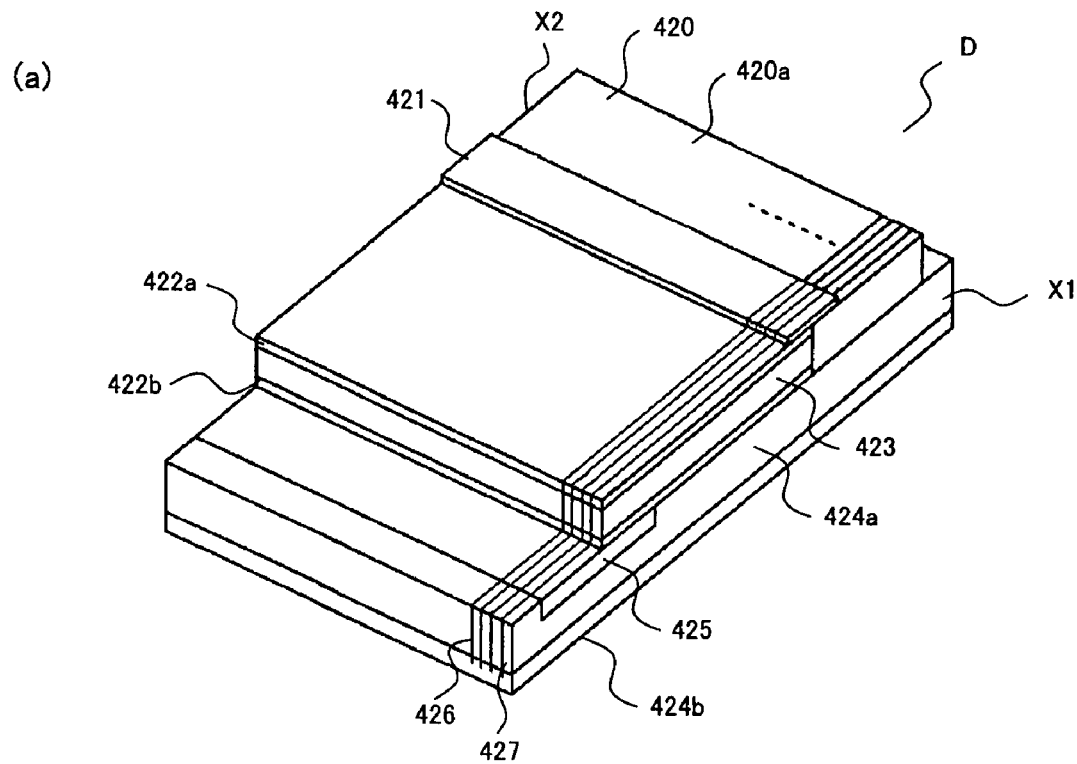
(a)
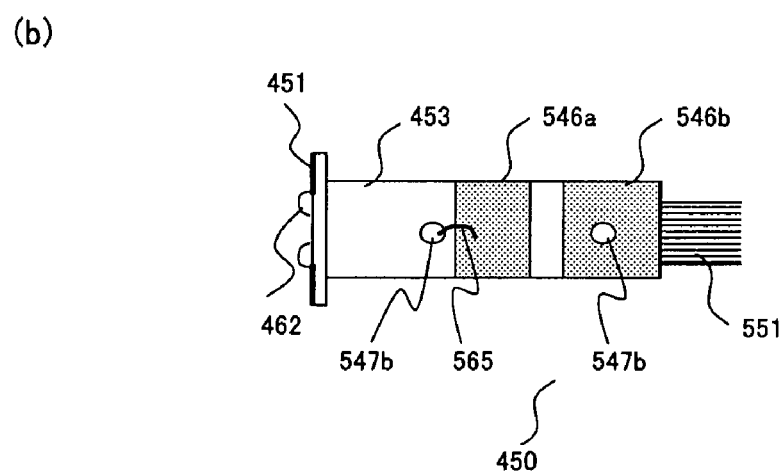
(b)
FIG. 40

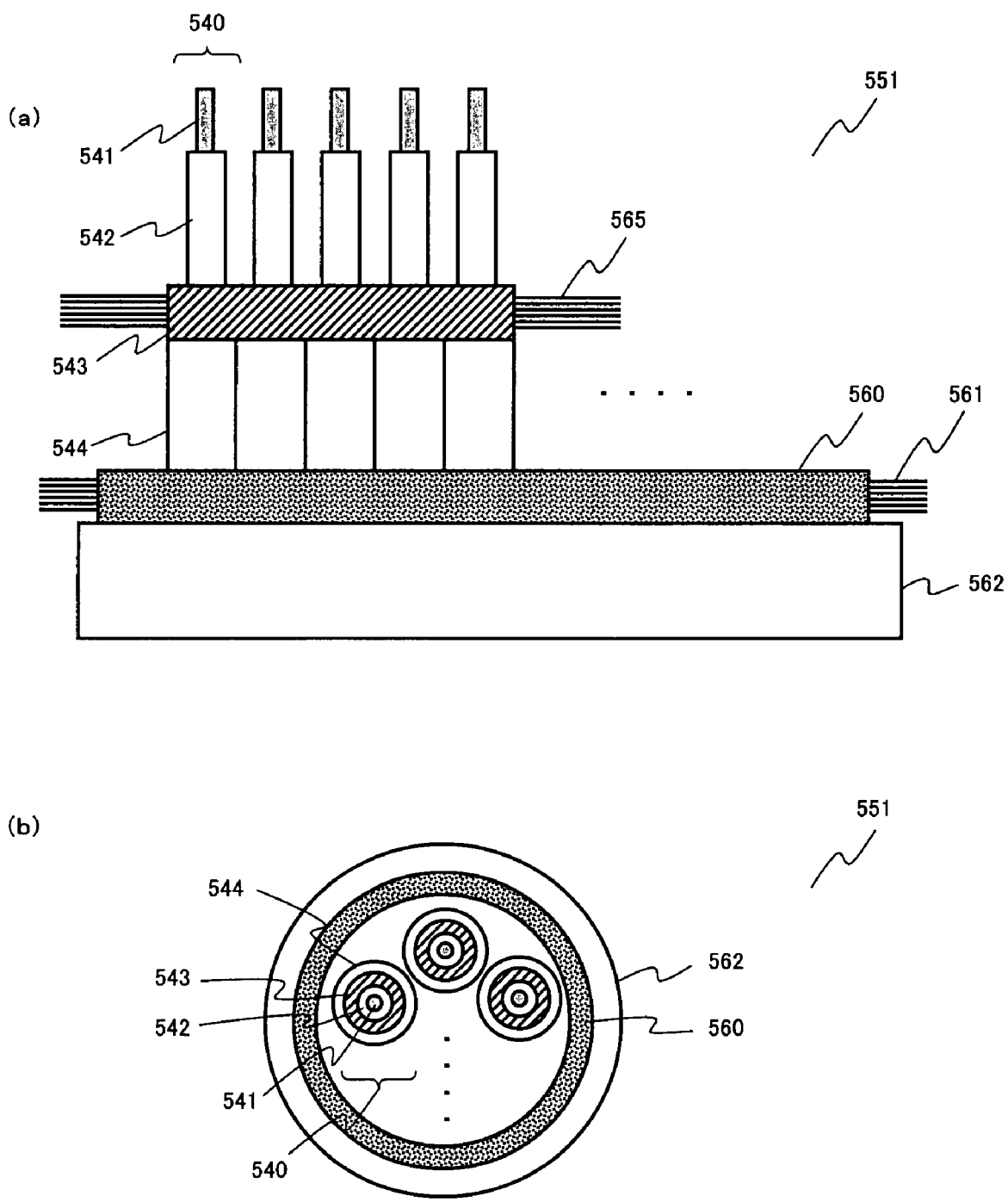
F I G. 4 2

ULTRASONIC PROBE

TECHNICAL FIELD

The present invention relates to an ultrasonic endoscope using an ultrasonic probe.

BACKGROUND ART

An ultrasonic endoscope, comprising an insertion unit for inserting the endoscope into an abdomen being equipped with an ultrasonic probe (i.e., an ultrasonic search unit), is capable of creating a clear image of a digestive canal wall and a deep organ, such as pancreas and gall bladder, in a good image quality without being influenced by an intra-abdomen gas, or a bone, by means of an ultrasonic beam transmitted/received from/to the ultrasonic probe.

Among those ultrasonic probes, one employing an electronic scanning system consists of tens of pieces of elements, in which each element must be connected to a transmission/reception-use coaxial cable. When connecting an electrode of each element of an electronic scanning ultrasonic probe to a signal transmission/reception-use coaxial cable, a common method is to solder a core lead of the coaxial cable to the signal electrode of each element and solder a shield wire of the coaxial cable to the ground electrode of each element. The tip of the insertion part of an endoscope is equipped with such configured ultrasonic probe.

Such ultrasonic endoscopes conventionally utilized include a convex type, a linear type and a radial type. Among them, the radial type is one transmitting/receiving (noted as "transceiving" (and "transceiver" as verb form) hereinafter) an ultrasonic beam in a circumferential direction, including a mechanical radial scanning system transceiving an ultrasonic beam in a radial pattern by rotating a probe and an electronic radial scanning system transceiving an ultrasonic beam in a radial pattern by means of arraying a plurality of piezoelectric elements on a circumference of a cylinder and an electronic control (e.g., refer to a patent document 1).

FIG. 1 is a diagram showing a conventional ultrasonic endoscope apparatus. The ultrasonic endoscope apparatus 160 shown in FIG. 1 comprises a connection part 161, an operation part 162 and an insertion part 163 which comprises a tip part 164.

The connection part 161 is for example connected to a display apparatus comprising a display in which an image photographed by an ultra compact camera equipped on the tip part 164 is displayed.

The operation part 162 performs an operation of curving the insertion part 163 in the up, down, left and right directions, that of expanding or contracting a balloon as described later, and other operations by a user operation.

The tip part 164 is equipped with an electronic radial array constituted by a plurality of ultrasonic transducer being continuously lined up circularly around the insertion axis as the center, in addition to the ultra compact camera, so that a predetermined ultrasonic transducer selected from among the plurality thereof transceives an ultrasonic wave. An ultrasonic wave received by the electronic radial array is also converted into an electric signal and displayed in the display, et cetera, as an image.

Incidentally, the radial array equipped on the tip part 164 includes a mechanical radial array in which a plurality of ultrasonic transducers is mechanically scanned, in addition to the electronic radial array (e.g., refer to a non-patent document 1).

FIG. 2 is an enlarged diagram of the dotted line circle A indicated in FIG. 1. As shown in FIG. 2, the tip part 164 comprises a camera part 170 equipped with the ultra compact camera, illumination, et cetera, and an ultrasonic part 171 equipped with the electronic radial array, et cetera.

FIG. 3 is a diagram exemplifying an electronic radial array. The radial array shown in FIG. 3 shows a state before individual ultrasonic transducers are formed into a circular form. The electronic radial array 180 comprises a piezoelectric element 181, an electrode 182, a first acoustic matching layer 183, a second acoustic matching layer 184, a conductive resin 185, a conductor body 186 and a substrate 187.

The piezoelectric element 181, electrode 182, first acoustic matching layer 183, second acoustic matching layer 184, conductive resin 185, conductor body 186 and substrate 187 are divided into a plurality thereof by commonly equipped grooves, resulting in comprising the plurality of ultrasonic transducers.

Then, the electronic radial array 180 is formed into a tubular form by the end surfaces in the direction perpendicular to the longitudinal direction of the electronic radial array 180 being connected to one another from the state shown in FIG. 3. Then, a lock member for locking an end of a later described balloon is mounted onto the opening part of the tubular-formed electronic radial array 180 on the side of the conductive resin 185.

Note that an ultrasonic endoscope shown in the non-patent document 1 is configured to equip the tip of a cap, which covers a mechanical radial array, with a groove to which an end of a balloon is locked.

FIG. 4 is a diagram exemplifying a lock member mounted onto an electronic radial array 11. As shown in FIG. 4, the lock member 190 is equipped with a lock groove 191 for fixing an end of a balloon.

FIG. 5 exemplifies a balloon. The balloon 200 shown in FIG. 5 is configured to be made of an elastic body such as an elastomer and formed to be tubular, and is mounted onto an ultrasonic part 171 so as to cover the electronic radial array 180.

FIG. 6 is a diagram showing how the balloon 200 is mounted onto the ultrasonic part 171. As shown in FIG. 6, one end of the opening of the balloon 200 is outserted onto a lock groove 210 featured between the camera part 170 and ultrasonic part 171, while the other end of the opening is outserted onto a lock groove 191, thereby the balloon being fixed so as to cover the electronic radial array 180.

Then, when internally filling the balloon with an ultrasonic medium 211 such as water in the state of the balloon 200 being mounted onto the ultrasonic part 171, the circumference of the electronic radial array 180 can be filled with the ultrasonic medium 211.

Thus filling of the balloon 200 with the ultrasonic medium 211 makes it possible to fill the circumference of the electronic radial array 180 with the ultrasonic medium 211, enabling an easy performance of an ultrasonic diagnosis or treatment at a spot where it is difficult to let an ultrasonic medium 211 stay, such as esophagus. It is also possible to perform an ultrasonic diagnosis or treatment in a narrow place within an abdomen because a predetermined space can be created between the electronic radial array 180 and human body by expanding the balloon 200.

In the case of constituting the ultrasonic part 171 by mounting the lock member 190 onto the electronic radial array 180 as described above, however, there is a risk of the lock member 190 falling out of the electronic radial array 180 if the connection part between the electronic radial array 180 and lock member 190 is damaged due to an unexpected physical, mechanical and/or electrical influence even though the electronic radial array 180 is attached to the lock member 190 by a strong adhesive.

FIG. 7 is a diagram showing a conventional ultrasonic endoscope apparatus. The ultrasonic endoscope apparatus 350 shown in FIG. 7 is an electronic scanning type ultrasonic endoscope apparatus, comprising a connection part 351, an operation part 352 and an insertion part 353 which comprises a tip part 354.

The connection part 351 is connected to a measurement apparatus comprising a display, for example, displaying an image obtained by an ultra compact camera equipped on the tip part 354.

The operation part 352 performs an operation of curving the insertion part 353 in up, down, left and right directions, for example, by a user operation.

The tip part 354 is equipped with an ultrasonic transducer array constituted by a plurality of ultrasonic transducer being continuously lined up, in addition to the ultra compact camera, so that a predetermined ultrasonic transducer selected from among the plurality thereof transceives an ultrasonic wave. An ultrasonic wave received by the ultrasonic transducer array is also converted into an electric signal and displayed in the display, et cetera, as an image.

FIG. 8 is an enlargement diagram of the tip part 354 shown in FIG. 7. As shown in FIG. 8, the tip part 354 comprises a scope part 355 having a photographing function such as ultra compact camera, illumination, et cetera, and the ultrasonic transducer array 356.

The ultrasonic transducer array 356 comprises an acoustic lens 357 equipped on the outside of a plurality of ultrasonic transducer, a balloon lock member 358, being equipped on one end of the acoustic lens 357, for locking an end of a later described balloon, and a scope connection member 359 equipped between the end of the acoustic lens 357 and the scope part 355.

As described above, the ultrasonic endoscope apparatus 350 is commonly used by mounting a balloon made of an elastomer onto the ultrasonic transducer array 356 (e.g., refer to a patent document 2).

FIG. 9 is a cross-sectional diagram of the ultrasonic transducer array 356 on which a balloon is mounted. In this diagram, the same component sign is assigned to the same configuration as one shown in FIG. 8. The balloon 360 shown in FIG. 9 is for example configured as a tube which is made of an elastic body as elastomer. One end of the opening of the balloon 360 is latched to a balloon lock groove 361 featured on the circumference of the scope part 355 while the other end of the opening of the balloon 360 is latched to an balloon locking groove 362 featured on the circumference of the balloon lock member 358, thereby the balloon 360 being mounted onto the ultrasonic transducer array 356 so as to cover the acoustic lens 357.

Then, when the balloon 360 is internally filled with an ultrasonic medium 363 such as water in the state of the balloon 360 being mounted onto the ultrasonic transducer array 356, the circumference of the acoustic lens 357 can be filled with the ultrasonic medium 363.

Thus filling of the balloon 360 with the ultrasonic medium 363 makes it possible to fill the circumference of the acoustic lens 357 with the ultrasonic medium 363, enabling an easy performance of an ultrasonic diagnosis or treatment at a spot where it is difficult to let an ultrasonic medium 363 stay, such as esophagus.

It is also possible to perform an ultrasonic diagnosis or treatment in a narrow place within an abdomen because a predetermined space can be created between the ultrasonic transducer array 356 and human body by expanding the balloon 363.

In the case of constituting the ultrasonic transducer array 356 by an acoustic lens 357, a balloon lock member 358 that is an endoscope structure member and a scope connection member 359, as the above noted ultrasonic endoscope apparatus 350, however, the acoustic lens 357 is generally structured by a soft material such as elastomer, while the balloon lock member 358 and scope connection member 359 are generally structured by a plastics, et cetera. As such, the acoustic lens 357 is structured by a different material than that of the balloon lock member 358 and scope connection member 359, and therefore the acoustic lens 357, balloon lock member 358 and scope connection member 359 cannot be integrally structured. Due to this, it is necessary to equip a connection band constituted by an adhesive, et cetera, between the acoustic lens 357 and balloon lock member 358, and also between the acoustic lens 357 and scope connection member 359, in order to connect the acoustic lens 357 to the balloon lock member 358, and connect the acoustic lens 357 to the scope connection member 359. If either of the both end parts of the acoustic lens 357 is featured to be protrusive than the balloon lock member 358 or scope connection member 359 in this event, such a protrusion causes the problem of the ends of the acoustic lens 357 becoming prone to receiving a force from the balloon 360, resulting in levying loads at the both ends of the acoustic lens 357, respectively, when mounting the balloon 360 onto the ultrasonic transducer array 356 or removing the balloon 360 therefrom.

And if the respective loads are levied at the both ends of the acoustic lens 357 at the time of mounting or removing the balloon 360, the caused problem includes the mounting or removal of the balloon 360 becoming difficult or the acoustic lens 357 peeling off.

And, it is necessary to consider the safety for a human body in designing an endoscope since it is an instrument to be inserted internally to a body cavity. Because the outer surfaces of the insertion part and its tip part (i.e., an ultrasonic probe) are covered with an insulative resin, the internal signal wire is not conceivably externally exposed.

If the plastics covering the outer surfaces are damaged, however, there is a possibility of the signal wire being externally exposed. In such an event, an electric shock can be avoided by the entirety of the signal wire being covered with a protective grounded metal.

Patent document 1: Japanese registered patent Sho 63-14623

Patent document 2: Japanese registered patent Hei 06-13034

Non-patent document 1: Electronic Industries Association of Japan (currently, Japan Electronics and Information Technology Industries Association): Handbook of Ultrasonic Diagnostic Equipments, pp. 114; published by Corona Publishing Co., Ltd.; Jan. 20, 1997

DISCLOSURE OF INVENTION

The present invention provides an ultrasonic probe capable of preventing a lock member from dropping off an electronic radial array due to an unexpected external force and a usage of a chemical agent with an unexpected attacking property.

In order to accomplish the provision as described above, an electronic radial ultrasonic probe according to a preferred embodiment of the present invention is one comprising an electronic radial array which comprises a plurality of ultrasonic transducers being continuously arrayed circularly around an insertion axis as center and also for which a transmission/reception of an ultrasonic wave is controlled by electronically selecting the plurality of ultrasonic transducer, comprising: a support member equipped on the electronic radial array; a lock member featured with a cavity in which the support member is inserted and with a lock groove for locking a balloon which is mounted in a manner to cover the electronic radial array and in which an ultrasonic medium is filled; and a filler member constituted by an adhesive material converting from a fluid state to a solid state, and is filled in the cavity.

The present invention also provides an ultrasonic endoscope apparatus and an ultrasonic transducer array which are capable of reducing a load applied to a connection part between an acoustic lens and an endoscope structure member at the time of mounting or removing a balloon.

In order to accomplish the provision as described above, an ultrasonic probe according another preferred embodiment of the present invention is one comprising an ultrasonic transducer array which comprises an acoustic lens equipped externally to a plurality of ultrasonic transducers that are continuously lined up and a balloon lock member for locking an end of a balloon, wherein an ultrasonic transducer selected from among the plurality thereof transmits or receives an ultrasonic wave, wherein an outer diameter of the balloon lock member at a part connecting to the acoustic lens is larger than that of the acoustic lens at a part connecting to the balloon lock member, and also the acoustic lens is connected to the balloon lock member by way of a connection band for smoothing out steps of the respective connection parts.

The present invention also provides an electronic radial ultrasonic probe having a protective grounding structure.

In order to accomplish the provision as described above, an electronic radial ultrasonic probe according another preferred embodiment of the present invention is one comprising first and second electrodes and lining up, in the form of a cylinder, a plurality of ultrasonic transducer elements for transmitting/receiving an ultrasonic wave by using a potential difference between the first and second electrodes, storing internally in the cylinder a group of cables corresponding to respective ultrasonic transducer elements for transmitting a drive signal for driving the individual ultrasonic transducer elements, and electrically connecting signal wires of the respective cables to the first electrode existing internally in the cylinder, wherein the ground wire included in the cable is connected to a first conductive body having approximately the same form as an opening which is mounted onto an opening of a cylindrical body formed by a group of the plurality of ultrasonic transducer elements that are lined up in the cylinder form.

BRIEF DESCRIPTION OF DRAWINGS

FIG. 1 is a diagram showing a conventional ultrasonic endoscope apparatus;

FIG. 4 is a diagram exemplifying a lock member;

FIG. 6 is a diagram showing a situation of mounting a balloon onto an ultrasonic part;

FIG. 21 is a diagram showing another example of a head part of an ultrasonic endoscope apparatus of a preferred embodiment of the present invention according to the first preferred embodiment (an embodiment 4 thereof);

FIG. 23 is a diagram showing another example of a head part of an ultrasonic endoscope apparatus of a preferred embodiment of the present invention according to the first preferred embodiment (an embodiment 4 thereof);

FIG. 24 is a diagram showing a situation of connecting a support member shown in FIG. 19 to a lock member equipped with a cavity shown in FIG. 11 according to the first preferred embodiment (an embodiment 4 thereof);

FIG. 30 is an enlarged diagram of a head part of an ultrasonic endoscope 401 shown in FIG. 29;

FIG. 32 is a diagram showing a production process (part 2) of an ultrasonic probe according to the third preferred embodiment (an embodiment 1 thereof);

FIG. 34 is a diagram showing a production process (part 4) of an ultrasonic probe according to the third preferred embodiment (an embodiment 1 thereof);

FIG. 38 is an enlarged diagram of a coaxial cable group 462 enclosed by a dotted line frame 530 indicated in FIG. 37;

FIG. 40 is a diagram showing a part of a production process of an ultrasonic probe according to the third preferred embodiment (an embodiment 2 thereof);

FIG. 42 shows an enlarged diagram of a part of a coaxial cable 551 which is enclosed by a dotted line frame 550.

BEST MODE FOR CARRYING OUT THE INVENTION

The following is a description of the preferred embodiment of the present invention by referring to the accompanying drawings.

First Embodiment

Embodiment 1

Figure 10:
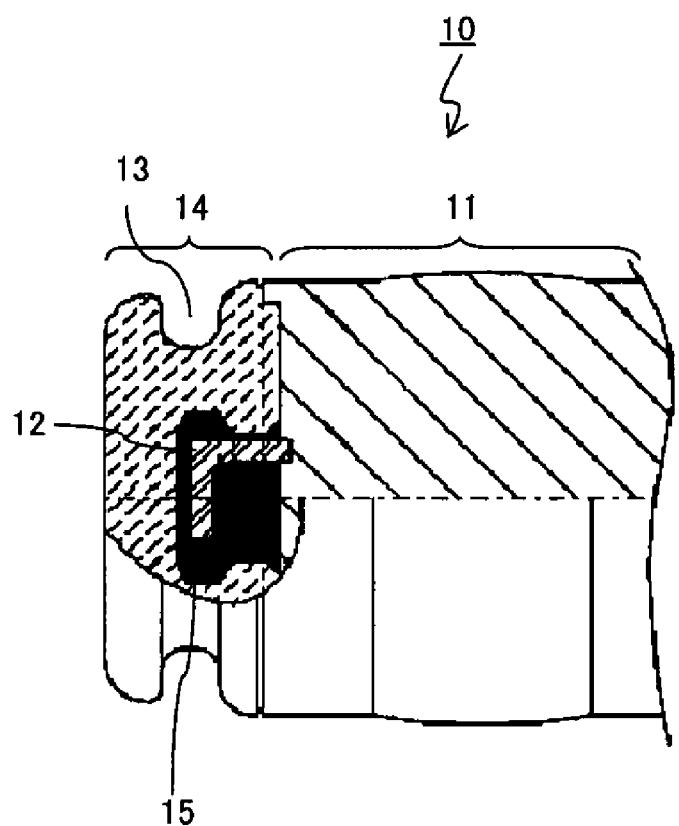
FIG. 10 is a diagram showing a head part of an ultrasonic endoscope apparatus according to a first preferred embodiment (an embodiment 1 thereof)

FIG. 10 is a diagram showing a head part of an ultrasonic endoscope apparatus according to the first embodiment. Note that the head part shown in FIG. 10 is a part corresponding to the tip part 164 of the ultrasonic endoscope apparatus 160 shown in FIG. 1.

The head part 10 shown in FIG. 10 mainly comprises an electronic radial array 11, a support member 12, a lock member 14 and a filler member 15. The electronic radial array 11 is configured by lining up a plurality of ultrasonic transducers in a ring pattern around an insertion axis as center. These ultrasonic transducers are electronically selected and a transmission/reception (noted as "transception" hereinafter) of an ultrasonic wave is controlled. The support member 12 is equipped on the electronic radial array 11 and formed as an approximate alphabet L, that is, featured with one overhang being featured at the head part. The lock member 14 is equipped with a cavity for inserting the support member 12 and with a lock groove 13. The lock groove 13 is for locking a balloon which is mounted in a manner to cover the electronic radial array 11 followed by filling the balloon with an ultrasonic medium. The filler member 15 is constituted by an adhesive material changing from a fluid state to a solid state (or, approximate rigid body) and is filled in the cavity.

Note that a method for connecting the support member 12 to the electronic radial array 11 may be by means of adhesion, riveting, brazing (i.e., welding, soldering, et cetera) and caulking, for example, in lieu of being limited to one method. Meanwhile, the connection strength of the support member to the electronic radial array 11 is desirably the same or higher as compared to the breakdown strength of either of the support member 12, lock member 14 or filler member 15 per se. The overhang formed on the side face of the support member 12 may be formed in the entirety or part of the circumference among the entirety of the side surface. The number of overhangs formed in the support member 12 may be two or more. In the case of forming two or more overhangs, they may be continuously formed or intermittently formed. And a position for mounting the support member 12 or lock member 14 to the electronic radial array 11 may be on the center axis thereof or off center. And the support member 12 may be formed in a hook form.

The support member 12 is configured to form approximately in the alphabet L as described above. Therefore, it is formed in a manner that the support member 12 is caught by the filler member 15 when the filler member 15 is converted into the solid state after the support member 12 is inserted into the filler member 15 in the fluid state within the cavity, that is, two certain cross-sectional area sizes and/or forms in the direction perpendicular to the insertion axis of the electronic radial array 11 are mutually different.

The cavity is formed in a manner that the lock member 14 is caught by the filler member 15 when the filler member 15 in the fluid state within the cavity is converted into the solid state, that is, two certain cross-sectional area sizes and/or forms in the direction perpendicular to the insertion axis of the electronic radial array 11 are mutually different.

Figure 11:
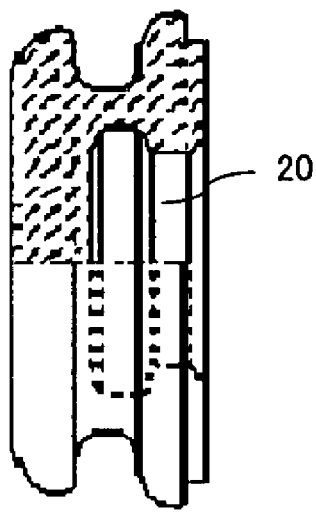
FIG. 11 is a diagram exemplifying a cavity featured in a lock member according to the first preferred embodiment (an embodiment 1 thereof)

FIG. 11 is a diagram exemplifying a cavity featured in the lock member 14 shown in FIG. 10. The cavity 20 of the lock member 14 shown in FIG. 11 is featured as an approximate mushroom form, that is, featured with one overhang in the internal side face. The opening part of the cavity 20 is featured in a manner to have a larger cross-sectional area size than that of the largest outer size of the support member 12 shown in FIG. 10.

Note that the cavity 20 may be formed together with other parts when the lock member 14 is produced by an injection molding or blow molding, or alternatively be processed by a lathe, et cetera, after molding the lock member 14. And, the overhang featured internally in the side face of the cavity 20 may be featured internally in the entirety or part of the internal circumference of the side face. The number of overhangs featured in the internal side face of the cavity 20 may be two of them or more. In the case of featuring two or more overhangs, they may be formed continuously or intermittently.

Figure 12:
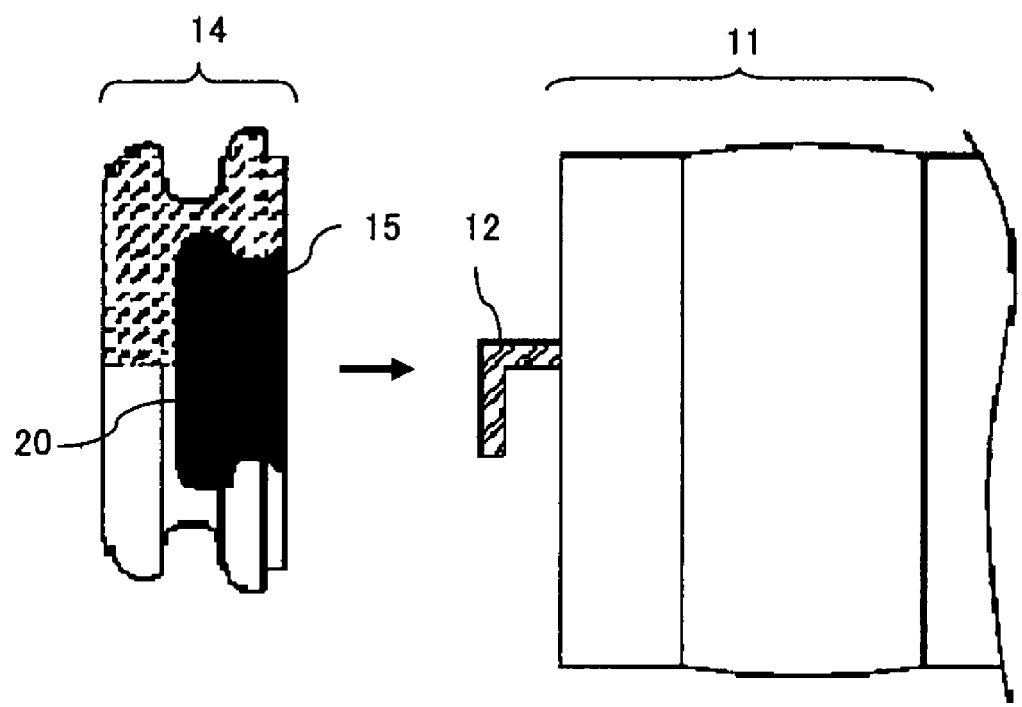
FIG. 12 is a diagram exemplifying a method for mounting a head part according to the first preferred embodiment (an embodiment 1 thereof)

The next is a description, by referring to FIG. 12, of an example method for mounting the head part 10 shown in FIG. 12.

FIG. 12 is a diagram exemplifying a method for mounting the head part 10 shown in FIG. 10. Incidentally, the same component sign is assigned to the same configuration as one shown in FIG. 10 or 11.

The first process fills the cavity 20 of the lock member 14 with an adhesive material (e.g., an organic solvent-series adhesive, elastic adhesive, epoxy resin-series adhesive, et cetera) as the filler member 15 and also applies an adhesive material to a circumference of the support member 12 (e.g., a surface thereof).

The next inserts the support member 12 into the adhesive material filled within the cavity 20 of the lock member 14 and assembles the electronic radial array 11 and lock member 14 together, followed by removing a run-over adhesive material from between the electronic radial array 11 and lock member 14 and letting the filled adhesive material set.

Note that an alternative configuration may be in a manner to assemble the electronic radial array 11 and lock member 14 and fill the cavity 20 with the filler material 15 from an injection hole featured in the lock member 14, followed by plugging the injection hole with an adhesive or resin following a completion of filling with the filler member 15.

As such, the support member 12 and lock member 14 are adhered together by the filler member 15 in the assembled head part 10, the support member 12 is further combined with the set (i.e., hardened) filler member 15 (i.e., the filler member 15 in the solid state) mechanically in a manner that the support member 12 is caught by the hardened filler member 15.

By this, the support member 12 and the hardened filler member 15 are mechanically combined together, and also the hardened filler member 15 and lock member 14 are mechanically combined together even if a damage is caused in between the electronic radial array 11 and lock member 14 by an unexpected external force or a use of a chemical agent with an unexpected attack property, resulting in a reduced strength at a part connecting the support member 12 or lock member 14 to the hardened filler member 15.

Because of this, even if the support member 12 or lock member 14 comes off the hardened filler material 15, the support member 12 and lock member 14 stay mechanically combined together by way of the hardened filler member 15 unless either of the lock member 14, hardened filler material 15 or support member 12 is broken, and therefore it is possible to prevent a situation of the lock member 14 falling off the electronic radial array 11, even if a damage is caused between the electronic radial array 11 and lock member 14 by an unexpected external force or a use of a chemical agent with an unexpected attack property.

Alternatively, the support member 12 may be formed by using a low x-ray transmission material such as metals, tungsten, or lead in order to enable an operator of an ultrasonic endoscope apparatus to externally confirming the position of the head part inserted into the inside of a human body.

By these, the operator is enabled to externally confirm the head part clearly by using an x-ray when it is inserted into the inside of a human body, and accordingly perform an easy guiding of an ultrasonic endoscope apparatus under a fluoroscopic control.

Alternatively, the support member 12 may be formed by a material containing a magnetic body in order for the operator of an ultrasonic endoscope apparatus to externally confirm a position of the head part 10 which is inserted into the inside of a human body by using a magnetic field detection apparatus (not shown herein).

Or, a coil may be wound around the support member 12 in order for the operator of an ultrasonic endoscope apparatus to externally confirm a position of the head part 10 which is inserted into the inside of a human body. This configuration is described in detail for an embodiment 2.

Embodiment 2

Figure 13:
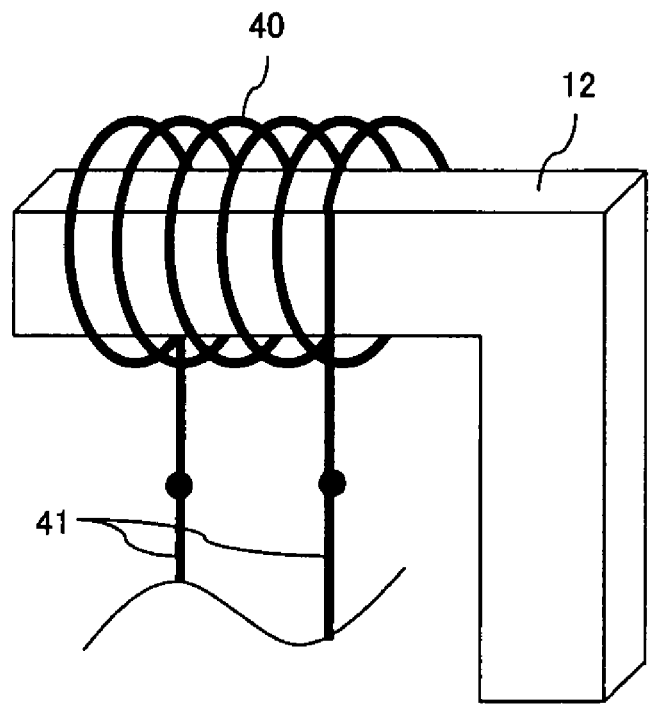
FIG. 13 is a diagram exemplifying a coil wound around a support member according to the first preferred embodiment (an embodiment 2 thereof)

FIG. 13 is a diagram exemplifying a coil wound around the support member 12 according to the first preferred embodiment (an embodiment 2 thereof). As shown in FIG. 13, the coil 40 is wound around the head part of the support member 12. Both ends of the coil 40 are respectively connected to coil signal wires 41.

An alternative configuration may be in a manner to output a high frequency signal to the coil signal wires 41, detect a magnetic field generated by the coil 40 and identify a position of the head part 10 based on the detected magnetic filed, for example.

Another configuration may be in a manner to apply a prescribed magnetic field to a spot where a diagnosis or treatment is carried out and identity a position of the head part 10 based on an output obtained from the coil 40 by way of the coil signal wire 41.

As described above, the forming of the support member 12 by a material with a low x-ray transmission property or material containing a magnetic body, or the wound coil 40 around the support member 12, makes it possible to obtain positional information for identifying the position of the head part 10 in the human baby. And the positional information can be used as diagnostic information used for guiding an insertion of an ultrasonic endoscope apparatus, matching a tomographic image with the human body atlas.

Figure 14:
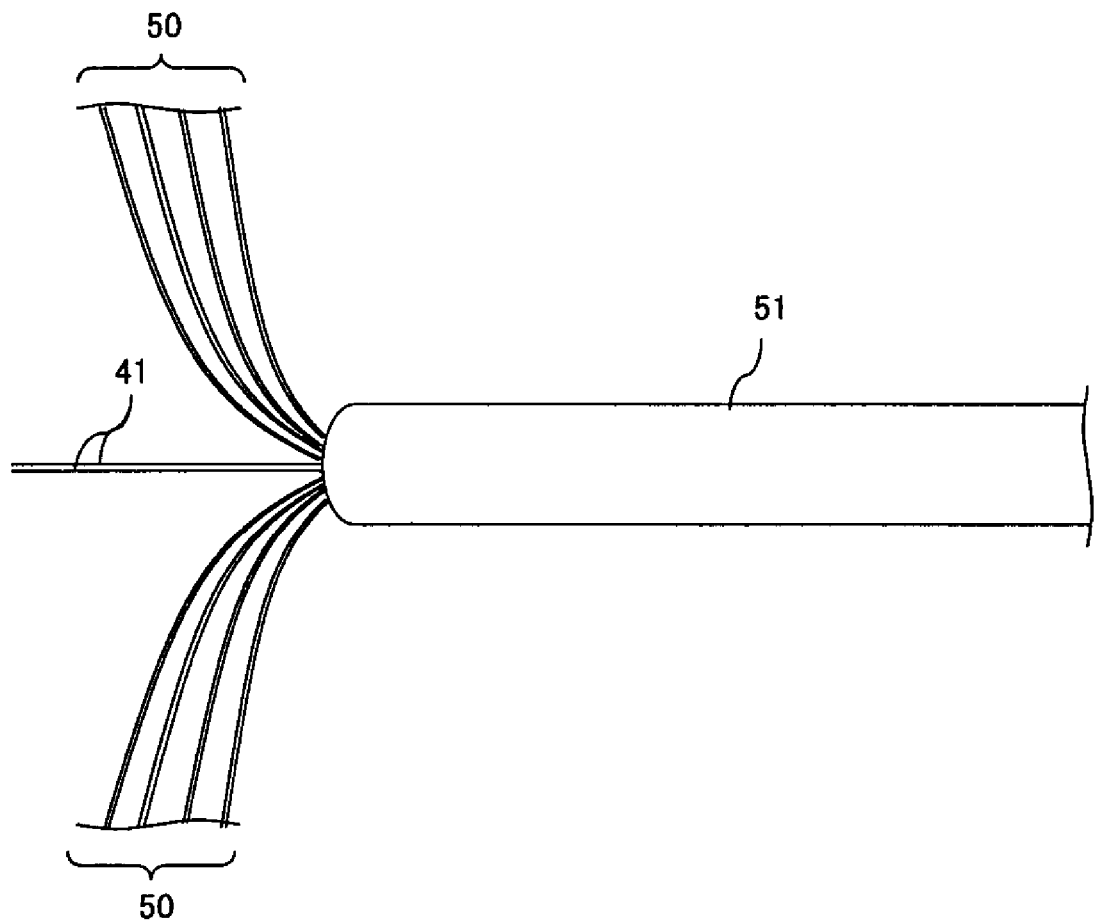
FIG. 14 is a diagram exemplifying a coil signal wire connected to a coil according to the first preferred embodiment (an embodiment 2 thereof)

FIG. 14 is a diagram exemplifying the coil signal wire 41 connected to the coil 40 shown in FIG. 13 according to the first preferred embodiment (an embodiment 2 thereof). Note that the same component sign is assigned to the same configuration as one shown in FIG. 13.

The coil signal wire 41 shown in FIG. 14 is bundled together with a plurality of signal wires 50 respectively connected to individual ultrasonic transducer of the electronic radial array 11 shown in FIG. 10 and led through a cable assembly 51.

Note that the coil signal wire 41 may be structured by the same coaxial cable as the signal wires 50, or a separate coaxial cable from the signal wire 50, or a lead wire.

As such, the structure of threading the coil signal wire 41 through the cable assembly 51 together with the signal wire 50 makes it possible to eliminate a work for harnessing the coil signal wire 41 in addition to the cable assembly 51 internally in the head part 10, thereby enabling a reduction of a work hour as that much when producing an ultrasonic endoscope apparatus.

Embodiment 3

The present invention can adopt various comprisals possible within the scope noted in claims herein, in lieu of being limited to the preferred embodiments described above. For example, a change of comprisals is viable as in the following.

Figure 15:
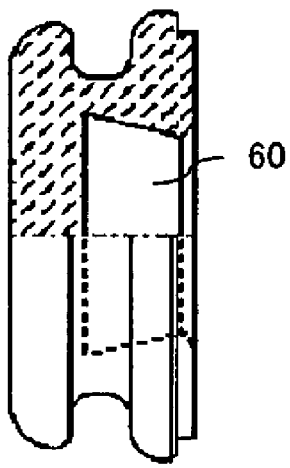
FIG. 15 is a diagram showing another example of a cavity featured in a lock member according to the first preferred embodiment (an embodiment 3 thereof)

FIG. 15 is a diagram showing another example of a cavity featured in a lock member 14 according to the first preferred embodiment (an embodiment 3 thereof). The cavity 60 of the lock member 14 shown in FIG. 15 is featured in an inverse taper form, that is, in a manner that the cross-sectional area size of the cavity 60 gradually increases with a depth toward the bottom side from the opening of the cavity 60. It is also configured that the opening part of the cavity 60 is featured to be larger than the largest cross-sectional area size in the support member 12 shown in FIG. 10, in the same manner as the cavity 20 shown in FIG. 11.

Figure 16:
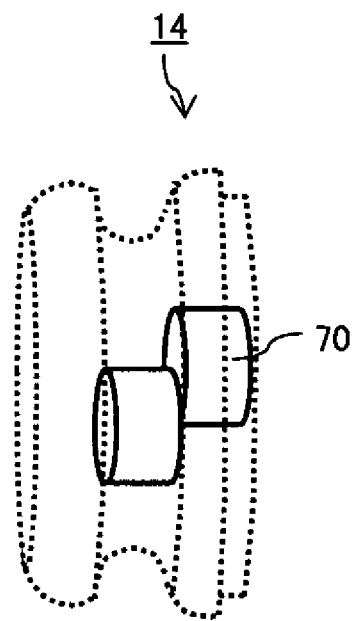
FIG. 16 is a diagram showing another example of a cavity featured in a lock member according to the first preferred embodiment (an embodiment 3 thereof)

FIG. 16 is a diagram showing yet another example of a cavity featured in a lock member 14 according to the first preferred embodiment (an embodiment 3 thereof). Note that FIG. 16 shows the external appearance by the dotted lines and the form of the cavity by the solid lines. The cavity 70 of the lock member 14 shown in FIG. 16 is formed in a manner that two columnar cavities having the same cross-sectional area size are stuck together with their center axes being displaced a little from each other. And the opening part of the cavity 70 is formed to be larger than the cross-sectional area size of the support member 12 shown in FIG. 10 in the thickest part, as in the case of the cavity 20 shown in FIG. 11.

Figure 17:
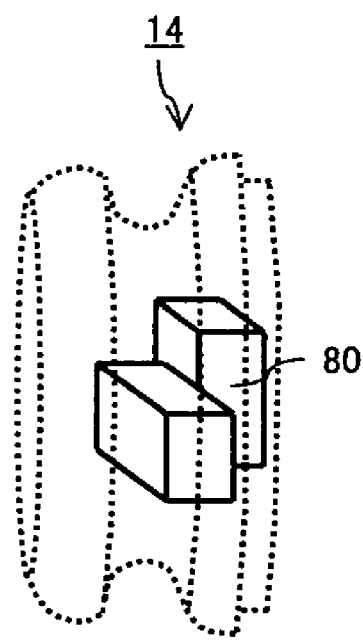
FIG. 17 is a diagram showing another example of a cavity featured in a lock member according to the first preferred embodiment (an embodiment 3 thereof)

FIG. 17 is a diagram showing yet another example of a cavity featured in a lock member 14 according to the first preferred embodiment (an embodiment 3 thereof). Note that FIG. 17 shows the external appearance by the dotted lines and the form of the cavity by the solid lines. The cavity 80 of the lock member 14 shown in FIG. 17 is formed in a manner that two rectangular cavities are stuck together by displacing from each other. And the opening part of the cavity 80 is formed to be larger than the cross-sectional area size of the support member 12 shown in FIG. 10 in the thickest part, as in the case of the cavity 20 shown in FIG. 11.

As described above, various forms of a cavity featured in the lock member 14 are conceivable.

Figure 18:
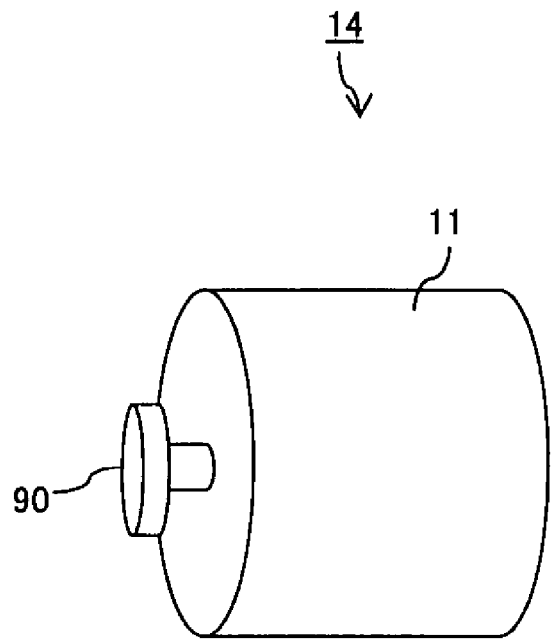
FIG. 18 is a diagram showing another example of a support member according to the first preferred embodiment (an embodiment 3 thereof)

FIG. 18 is a diagram showing yet another example of a support member 12 according to the first preferred embodiment (an embodiment 3 thereof). The support member 90 shown in FIG. 18 is formed in a manner that two column forms having different cross-sectional area sizes are stuck with each other.

Figure 19:
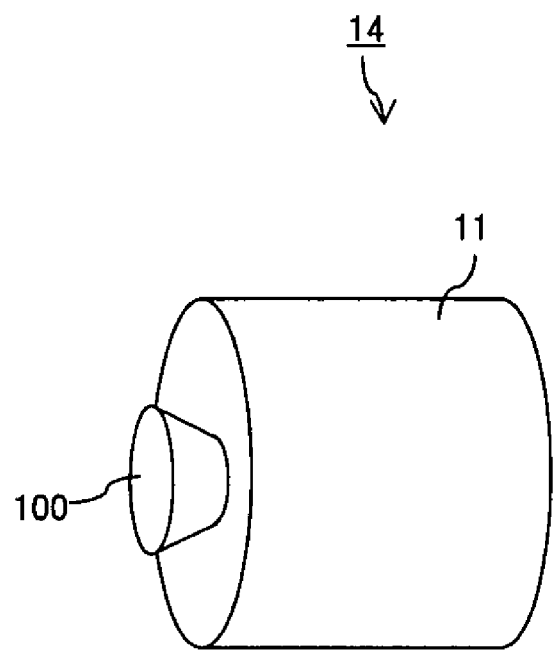
FIG. 19 is a diagram showing another example of a support member according to the first preferred embodiment (an embodiment 3 thereof)

FIG. 19 is a diagram showing yet another example of a support member 12 according to the first preferred embodiment (an embodiment 3 thereof). The support member 100 shown in FIG. 19 is formed in an inverse taper form, i.e., in a manner that the cross-sectional area size gradually increase toward the tip part.

Figure 20:
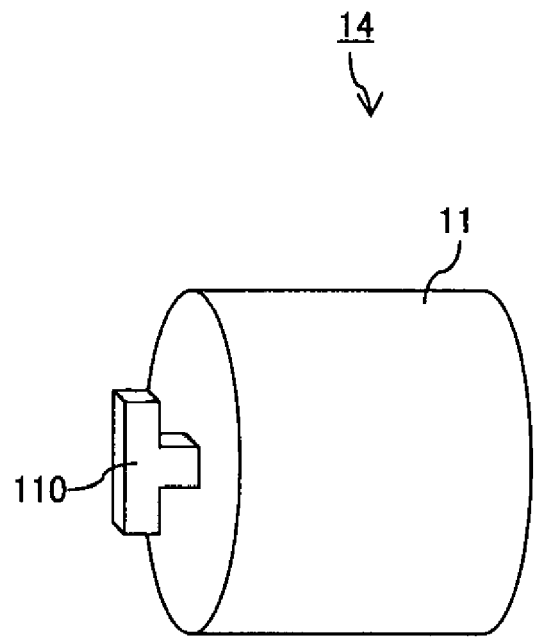
FIG. 20 is a diagram showing another example of a support member according to the first preferred embodiment (an embodiment 3 thereof)

FIG. 20 is a diagram showing yet another example of a support member 12 according to the first preferred embodiment (an embodiment 3 thereof). The support member 110 shown in FIG. 20 is in a manner that two rectangles are stuck with each other, that is, in an approximate alphabet T.

As described above, various forms of the support member 12 are also conceivable.

Embodiment 4

FIG. 21 is a diagram showing another example of a head part of an ultrasonic endoscope apparatus according to the first preferred embodiment (an embodiment 4 thereof). Note that the head part shown in FIG. 21 is the part corresponding to the tip part 164 of the ultrasonic endoscope apparatus 160 shown in FIG. 1. Also, the same component sign is assigned to the same constituent component as one shown in FIG. 10.

The characteristic of the head part 120 shown in FIG. 21 lies in comprising a support member 121 equipped in the head part of an electronic radial array 11 and featured with a screw on the side face, a cavity featured with a screw corresponding to the screw on the support member 121 internally in the inside face, and a lock member 123 featured with a lock groove 122 for locking with an end of a balloon which is mounted in a manner to cover the electronic radial array 11 and also filled with an ultrasonic medium, in which the support member 121 and the lock member 123 are connected to each other by tightening the screw between the support member 121 and the cavity.

Thus connecting by the screw enables a direct mechanical connection of the support member 121 to the lock member 123, thereby reducing a work load, et cetera, for positioning when producing an ultrasonic endoscope apparatus.

Figure 22:
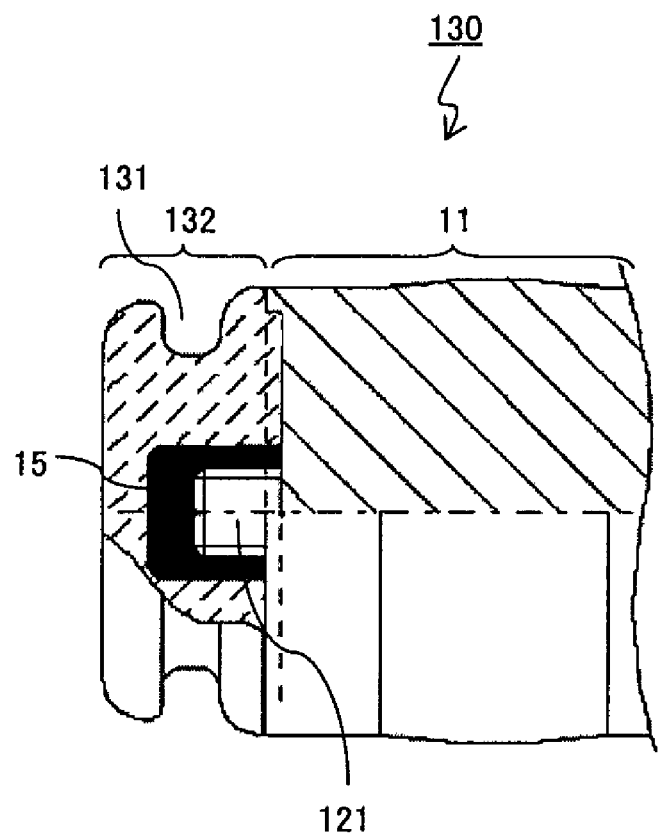
FIG. 22 is a diagram showing another example of a head part of an ultrasonic endoscope apparatus of a preferred embodiment of the present invention according to the first preferred embodiment (an embodiment 4 thereof)

FIG. 22 is a diagram showing another example of a head part of an ultrasonic endoscope apparatus according to the first preferred embodiment (an embodiment 4 thereof). Note that the head part shown in FIG. 22 is the part corresponding to the tip part 164 of the ultrasonic endoscope apparatus 160 shown in FIG. 1. Also, the same component sign is assigned to the same constituent component as one shown in FIG. 10 or 21.

The head part 130 shown in FIG. 22 comprises a support member 121, a lock member 132, and a filler member 15. The support member 121 is the same as one shown in FIG. 21. The lock member 132 is featured with a cavity having a larger capacity than the support member 121 and with a screw internally in the side face, and a lock groove 131 for locking with an end of a balloon which is mounted in a manner to cover the electronic radial array 11 and also filled with an ultrasonic medium.

This comprisal also connects the support member 121 to the lock member 132 mechanically, and therefore is capable of preventing a situation of the lock member 132 dropping off the electronic radial array 11.

FIG. 23 is a diagram showing another example of a head part of an ultrasonic endoscope apparatus according to the first preferred embodiment (an embodiment 4 thereof). Note that the head part shown in FIG. 23 is the part corresponding to the tip part 164 of the ultrasonic endoscope apparatus 160 shown in FIG. 1. Also, the same component sign is assigned to the same constituent component as one shown in FIG. 10, 11 or 21.

The characteristic of the head part 140 shown in FIG. 23 lies in comprising a support member 121 shown in FIG. 21 and a lock member 14 equipped with a cavity 20 shown in FIG. 11, in which the support member 121 and lock member 14 are connected by a filler member 15.

This comprisal also enables a mechanical connection of the support member 121 to the lock member 14, and therefore is capable of preventing a situation of the lock member 14 dropping off the electronic radial array 11.

While a connection method between the electronic radial array 11 and support member 12 can conceivably use adhesion, riveting, grazing, caulking, et cetera, as described above, and the following connection method can also be considered.

FIG. 24 is a diagram exemplifying a method for connecting the support member 12 to electronic radial array 11 according to the first preferred embodiment (an embodiment 4 thereof). Note that FIG. 24 shows the situation of connecting the support member 100 shown in FIG. 19 to the lock member 14 featured with the cavity 20 shown in FIG. 11.

The support member 100 shown in FIG. 24 is featured with a hole 150 along the center axis thereof.

First step laces a rope-like member 151 (e.g., made of a high strength fiber such as aramid fiber and carbon fiber) through a cable assembly 51 shown in FIG. 14, et cetera, in advance.

The next laces the rope-like member 151 sticking out on the lock member 14 side from the cable assembly 51 through the hole 150.

The next attaches a knot 152 to the end of the rope-like member 151 sticking out to the tip side of the support member 100 after going through the hole 150.

By this, the knot 152 fixes the support member 100, thereby making it possible to connect the support member to the electronic radial array 11.

The above described embodiment is configured to wind the coil 40 around the support member 12 of an approximate alphabet L form; the coil 40, however, may be wound around the support member 110 which is formed in an approximate alphabet T as shown in FIG. 20, and a form of a support member for winding the coil 40 around is not particularly limited.

Also, the above described embodiment is configured to mount the lock member 14 onto the electronic radial array 11 as a result of combining the support member 12 and lock member 14 together through the filler member 15; the electronic radial array 11 and lock member 14, however, may alternatively be combined together by the filler member 15 directly.

For example, first, the lock member 14 is featured with the cavity 20 shown in FIG. 11 and also the support member 12 shown in FIG. 10 is made by using the filler member 15, and the head part of the electronic radial array 11 is equipped with the support member 12. Incidentally, the electronic radial array 11 and support member 12 may be connected together by the rope-like member 151 as described above, for example.

The next fills the cavity 20 with the filler member 15, which has been used when making the support member 12, and also coats the filler member 15 around the support member 12 made by the filler member 15.

The next inserts the support member 12 into the cavity 20, and assembles the electronic radial array 11 and lock member 14 together.

Then, when the filler member 15, et cetera, filled in the cavity 20 is hardened, the support member 12 and lock member 14 are mechanically combined together as if the one is caught by the other.

This configuration makes it possible to prevent a situation of the lock member 14 dropping off the electronic radial array 11 because the support member 12 is mechanically connected to the lock member 14 even if a damage is caused between the electronic radial array 11 and lock member 14 by an unexpected external force or use of a chemical agent having an unexpected attacking property, et cetera, resulting in a reduced strength of the connection part between the support member 12 and lock member 14.

As described thus far, the first embodiment of the present invention is configured in a manner that, when the filler member is converted into a solid state, the support member is adhered to the lock member by the filler member and, further, the support member is mechanically connected to the filler member as if the former is caught by the latter, and therefore the support member is mechanically connected to the filler member, and the lock member is mechanically connected to the filler member even if a damage is caused between the electronic radial array and lock member by an unexpected external force or use of a chemical agent having an unexpected attacking property, et cetera, resulting in a reduced strength of the connection part between the support member, or lock member, and the filler member.

By this, even if the support member or lock member comes off the filler member, the support member is continued to be mechanically connected to the lock member by way of the filler member unless either of the lock member, filler member or support member is broken, and therefore it is possible to prevent a situation of the lock member dropping off the electronic radial array even if a damage is caused between the electronic radial array and lock member by an unexpected external force or use of a medicine having an unexpected attacking property, et cetera.

Second Preferred Embodiment

The following is a description of a preferred embodiment of the present invention by using the accompanying drawings.

Embodiment 1

Figure 25:
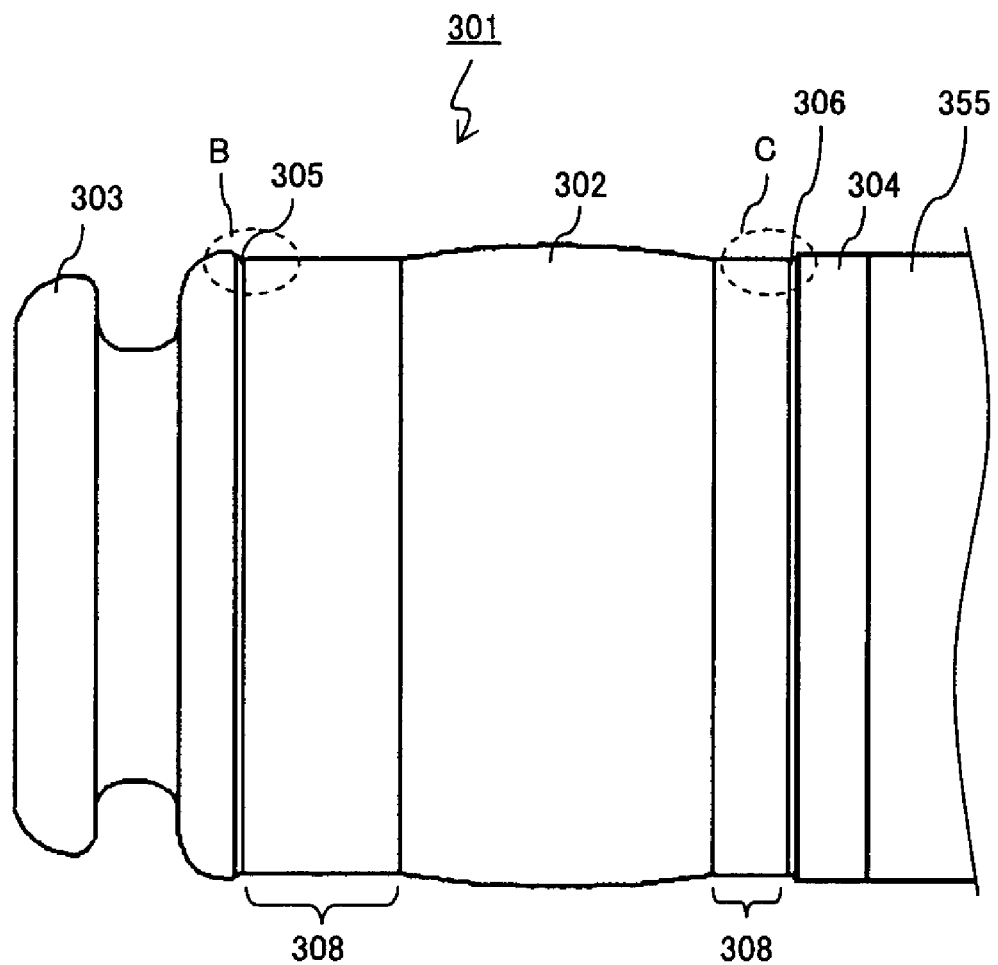
FIG. 25 is a diagram showing an ultrasonic transducer array comprised by an ultrasonic endoscope apparatus according to a second preferred embodiment (an embodiment 1 thereof)

FIG. 25 is a diagram showing an ultrasonic transducer array comprised by an ultrasonic endoscope apparatus according to a second preferred embodiment (an embodiment 1 thereof). Note that the same component sign is assigned to the same comprisal as one shown in FIG. 8.

Figure 2:
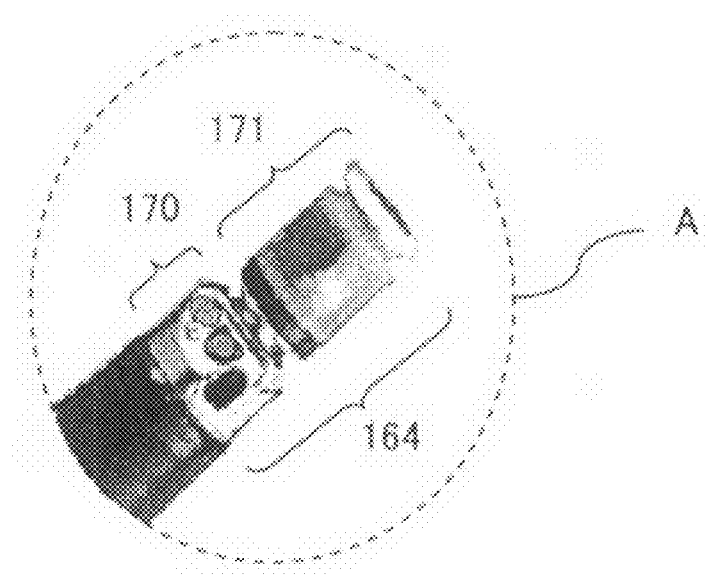
FIG. 2 is an enlarged diagram of a dotted line frame A.
Figure 3:
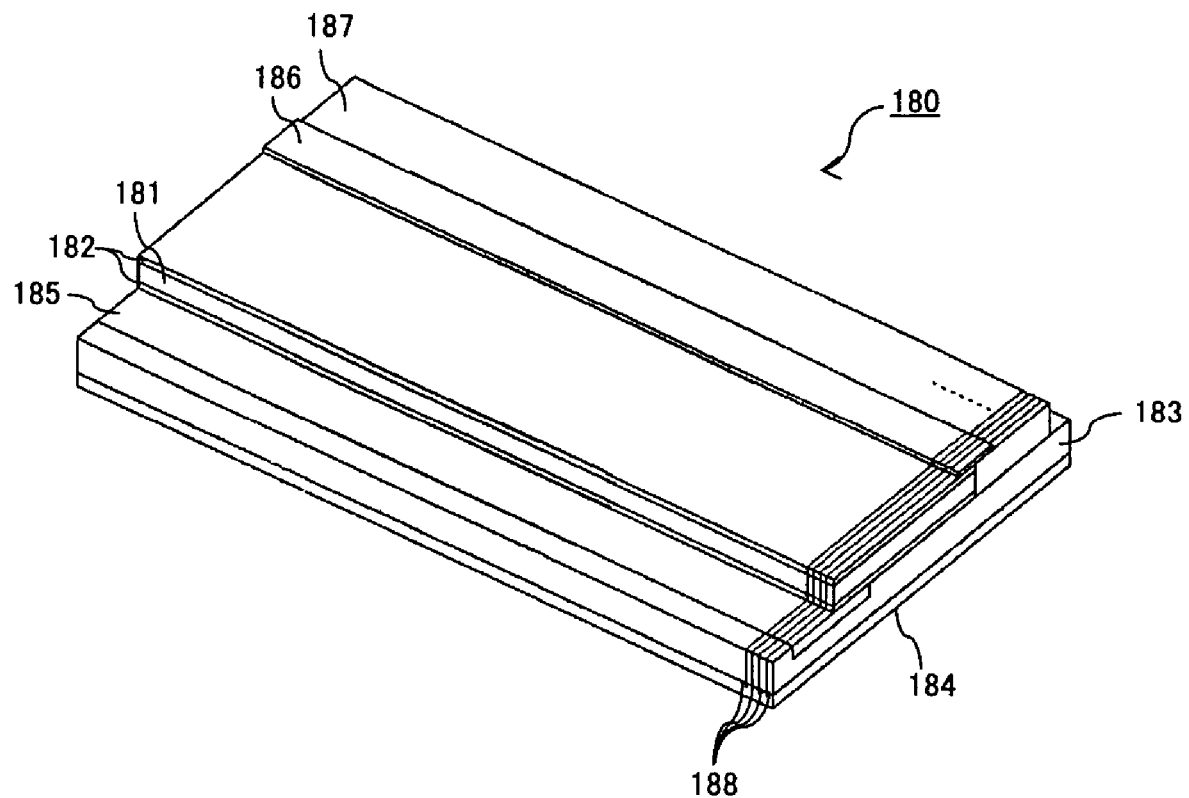
FIG. 3 is a diagram exemplifying an electronic radial array.
Figure 5:
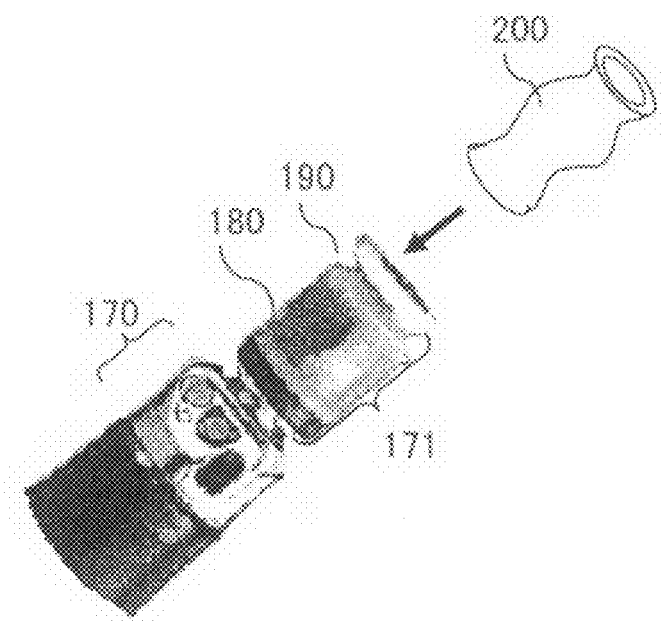
FIG. 5 is a diagram exemplifying a balloon.
Figure 7:
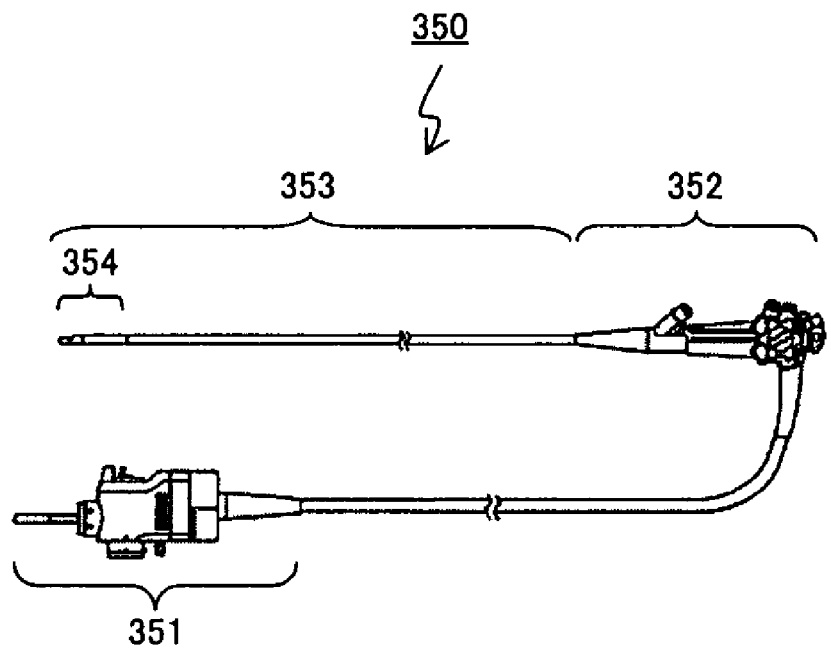
FIG. 7 is a diagram showing a conventional ultrasonic endoscope apparatus.
Figure 8:
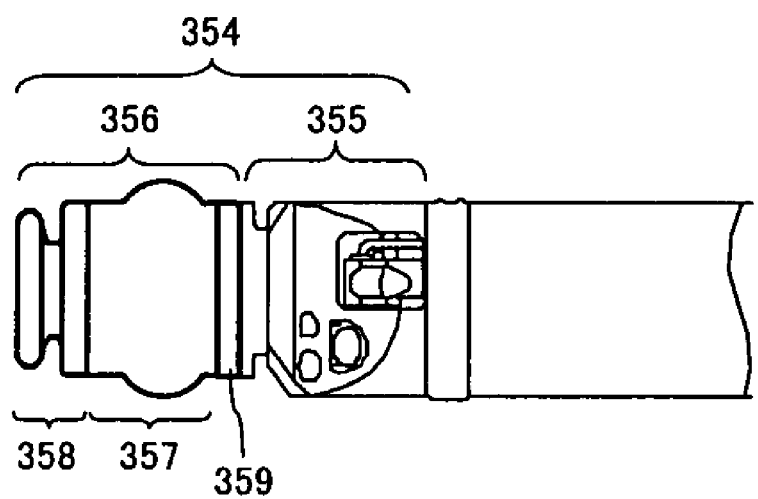
FIG. 8 is an enlarged diagram of a tip part.

The ultrasonic transducer array 301 shown in FIG. 25, being a comprisal to be equipped on the tip of a scope part 355 as in the case of the ultrasonic transducer array 356 shown in FIG. 8, comprises an acoustic lens 302, a balloon lock member 303 and a scope connection member 304.

In between the acoustic lens 302 and balloon lock member 303 is equipped with a connection band 305 constituted by an adhesive, et cetera. And in between the acoustic lens 302 and scope connection member 304 is equipped with a connection band 306 constituted by an adhesive, et cetera.

The characteristic of the aforementioned ultrasonic transducer array 301 lies where respective outer diameters of individual connection parts connected to the acoustic lens 302 are configured to be larger than respective outer diameters of individual connection parts connected to the balloon lock member 303 and scope connection member 304, respectively, of the acoustic lens 302 in both members of the balloon lock member 303 and scope connection member 304 that are endoscope structure members, and where the acoustic lens 302 is connected to the balloon lock member 303 by way of the connection band 305 for smoothing out a step between the acoustic lens 302 and balloon lock member 303, and also the acoustic lens 302 is connected to the scope connection member 304 by way of the connection band 306 for smoothing out a step between the acoustic lens 302 and scope connection member 304.

That is, the acoustic lens 302 and balloon lock member 303 are respectively formed in a manner that an outer diameter of a first member connection part of the balloon lock member 303 that is the connection part with the acoustic lens 302 is larger than an outer diameter of a first lens connection part of the acoustic lens 302 that is the connection part with the balloon lock member 303. Also configured is, the acoustic lens 302 is connected to the balloon lock member 303 by way of the connection band 305 of which the surface is processed to have a gradual tapered surface so as to eliminate the step between the first lens connection part and first member connection part.

Figure 26:
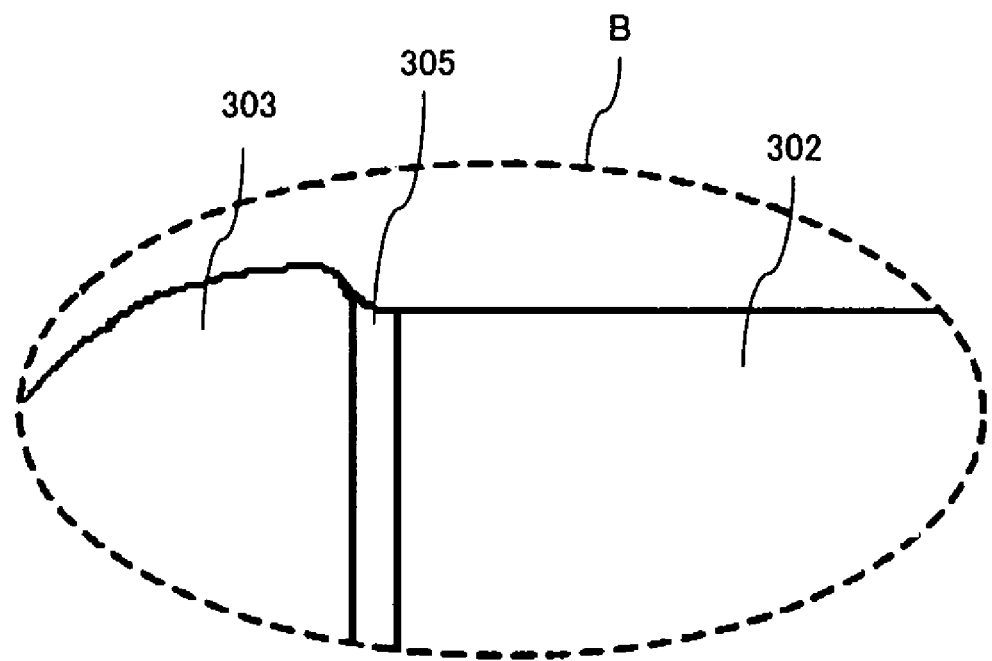
FIG. 26 is an enlarged diagram of a neighborhood of a part connecting a balloon lock member to an acoustic lens according to the second preferred embodiment (an embodiment 1 thereof)

FIG. 26 is an enlarged diagram of a dotted line frame B shown in FIG. 25, that is, an enlarged diagram of a neighborhood of a part connecting the balloon lock member 303 to the acoustic lens 302. As shown in FIG. 26, the edge of the balloon lock member 303 (i.e., the first member connection part) is projected outward than the edge of the acoustic lens 302 (i.e., the first lens connection part). And the edge of the acoustic lens 302 is connected to that of the balloon lock member 303 by way of the connection band 305 having a surface of a gradual slope.

At this point, the description exemplifies methods for connecting the acoustic lens 302, connection band 305 and balloon lock member 303, respectively.

The first step applies a surface treatment, by means of a chemical coating, corona discharge, gas, plasma, et cetera, to a surface of the acoustic lens 302 connecting to the balloon lock member 303 and that of the balloon lock member 303 connecting to the acoustic lens 302, respectively, so as to improve the respective coating properties of the connection band 305. The next coats the connection band 305 to each connecting surface and connects the acoustic lens 302 to the balloon lock member 303. The next processes the surface of the connection band 305 to a gradual slope by wiping the surface and/or smoothes it out.

Meanwhile, the acoustic lens 302 and scope connection member 304 are respectively formed so that an outer diameter of a second connection part of the scope connection member 304 that is the connection part with the acoustic lens 302 is larger than an outer diameter of a second lens connection part of the acoustic lens 302 that is the connection part with the scope connection member 304. Also configured is, the acoustic lens 302 is connected to the scope connection member 304 by way of the connection band 306 and the surface of the connection band 306 is processed to be a gradual slope so as to eliminate steps of the second lens connection part and second member connection part.

Figure 27:
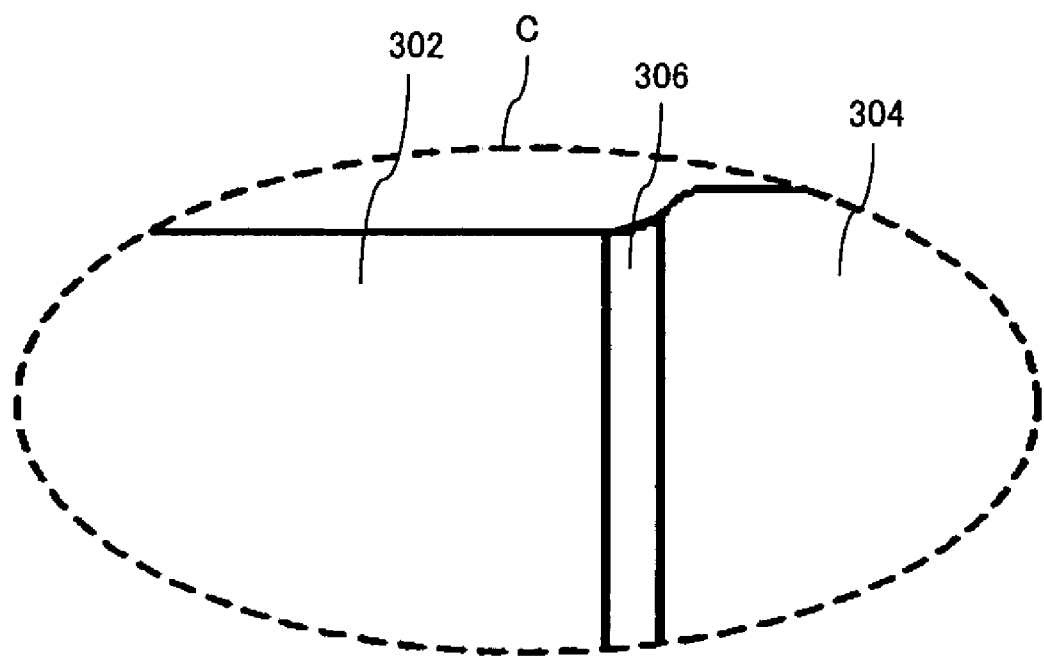
FIG. 27 is an enlarged diagram of a neighborhood of a part connecting a scope connection member to an acoustic lens according to the second preferred embodiment (an embodiment 1 thereof)

FIG. 27 is an enlarged diagram of the dotted line frame C shown in FIG. 25, that is, an enlarged diagram of a neighborhood of a part connecting the scope connection member 304 to the acoustic lens 302. As shown in FIG. 27, the edge of the scope connection member 304 (i.e., the second member connection part) is projected outward than that of the acoustic lens 302 (i.e., the second lens connection part). And the edge of the acoustic lens 302 is connected to that of the scope connection member 304 by way of the connection band 306 having a gradual slope surface.

At this point, a description exemplifies methods for connecting the acoustic lens 302, connection band 306 and scope connection member 304, respectively.

The first step applies a surface treatment, by means of a chemical coating, corona discharge, gas, plasma, et cetera, to a surface of the acoustic lens 302 connecting to the scope connection member 304 and that of the scope connection member 304 connecting to the acoustic lens 302, respectively, so as to improve the respective coating properties of the connection band 306. The next coats the connection band 306 to each connecting surface and connects the acoustic lens 302 to the scope connection member 304. The next processes the surface of the connection band 306 to a gradual slope by wiping the surface and/or smoothes it out.

Materials constituting the balloon lock member 303 and scope connection member 304 conceivably includes the following. As to resins for example, the conceivable is organic materials such as silicone series, epoxy series, PEEK (Registered Trademark), polyimide, polyether imide, polysulfone, polyether sulfone, fluorine series resin, et cetera. Also conceivable are aforementioned organic materials mixed with powder or fibers of a metal, ceramics, glass, carbon, et cetera. As to metals for example, the conceivable are stainless steel, titanium and its alloy, metallic glass, et cetera. And, as to inorganic materials, the conceivable are ceramics made of alumina, zirconia, silicon nitride, et cetera.

Also, materials constituting the acoustic lens 302 and a later described acoustic lens 309 conceivably includes as follows. The conceivable includes elastomer such as silicone series, urethane series, et cetera. Also conceivable are the aforementioned elastomer mixed with powder or fibers of metal, ceramics, glass, carbon, et cetera.

As to materials of the connection bands 305 and 306, conceivable includes as follows. The conceivable for example are adhesives of epoxy series, silicone series, urethane series, et cetera. Also conceivable are the aforementioned adhesive mixed with powder or fiber of a metal, ceramics, glass, carbon, et cetera.

Figure 9:
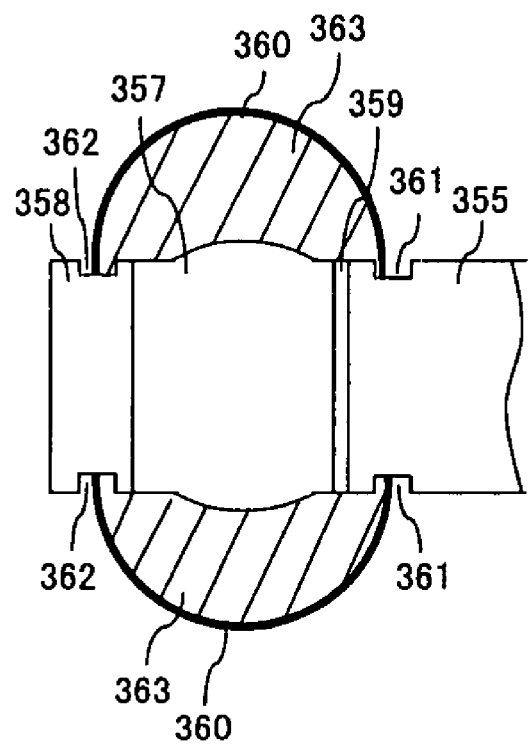
FIG. 9 is a cross-sectional diagram of an ultrasonic transducer array on which a balloon is mounted.

The aforementioned embodiment is configured in a manner that the outer diameters of the respective connection parts with the acoustic lens 302 is larger than the outer diameters of the respective connection parts connecting the acoustic lens 302 to the balloon lock member 303 and scope connection member 304, respectively, in both of the members of the balloon lock member 303 and scope connection member 304, and also both of the members of the balloon lock member 303 and scope connection member 304 are connected to the acoustic lens 302 by way of the connection bands 305 and 306 for smoothing out the respective steps of both of the members of balloon lock member 303 and scope connection member 304 with the acoustic lens 302. Therefore, this configuration hardly allows the balloon 360 as shown in FIG. 9 to be caught by the acoustic lens 357 as a result of the balloon 360 being guided by the connection bands 305 and 306 when mounting the balloon 360 onto the ultrasonic transducer array 301 or when removing the balloon 360 therefrom. This configuration reduces a load levied to the acoustic lens 357, thereby making it possible to mount or remove the balloon 360 smoothly.

The above described embodiment is also configured so as to enable a smooth mounting or removal of the balloon 360 without the edge of the acoustic lens 357 substantially catching the balloon 360 although it brushes a surface of the ultrasonic transducer array 301 when mounting or removing the balloon 360, thereby reducing a force applied to the end of the acoustic lens 302. This configuration makes it possible to prevent the acoustic lens 302 from peeling off the ultrasonic transducer array 301 or from being damaged at the time of mounting or removing the balloon 360.

Also, the above described embodiment makes it possible to let an air bubble out of the balloon 360 smoothly because the air bubble is hardly be caught by the connection bands 305 and 306 when letting the air bubble within the balloon 360 out thereof after mounting it onto the ultrasonic transducer array 301 and expand it with water, et cetera.

Also, the above described embodiment makes it possible to pass the balloon lock member 303, which has an outer diameter larger than that of the edge of the acoustic lens 302, through an insertion path of a human body in advance of the acoustic lens 302 when inserting the ultrasonic transducer array 301 into the human body. This enables the balloon lock member 303 to remove a foreign material, et cetera, in the insertion path of a human body and therefore the acoustic lens 302 can be protected from the foreign material, et cetera.

Note that the acoustic lens 302 according to the aforementioned embodiment is configured to equip with flat parts 308, each of which is called a shoulder, on the front and rear of the acoustic lens 302 as shown in FIG. 25; an ultrasonic endoscope apparatus may be configured by using an acoustic lens equipped with no flat part 308, however.

Embodiment 2

Figure 28:
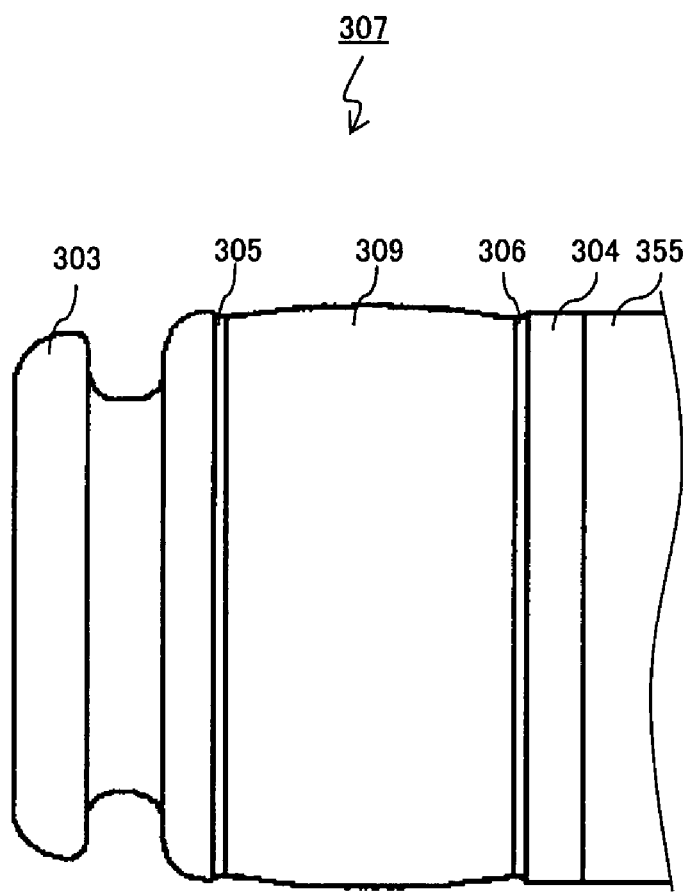
FIG. 28 is a diagram showing an ultrasonic transducer array comprised by an ultrasonic endoscope apparatus according to the second preferred embodiment (an embodiment 2 thereof)

FIG. 28 is a diagram showing an ultrasonic transducer array comprised by an ultrasonic endoscope apparatus according to the second preferred embodiment (the embodiment 2 thereof). Note that the same component sign is assigned to the same comprisal as one shown in FIG. 25.

The ultrasonic transducer array 307 shown in FIG. 28 comprises an acoustic lens 309 equipped with no flat part 308 as shown in FIG. 25.

And a connection band 305 constituted by an adhesive, et cetera, is equipped in between the acoustic lens 309 and balloon lock member 303. And a connection band 306 constituted by an adhesive, et cetera, is equipped in between the acoustic lens 309 and scope connection member 304. Note that the acoustic lens 309 may be equipped with a flat part 308 as shown in FIG. 25 on either of the edges.

The aforementioned ultrasonic transducer array 307 is configured in a manner that, in both of the members of the balloon lock member 303 and scope connection member 304 which are endoscope structure members, the respective outer diameters of individual connection parts with the acoustic lens 309 are larger than the respective outer diameters of the acoustic lens 309 at individual parts for connecting to the balloon lock member 303 and scope connection member 304. Also configured is, both members of the balloon lock member 303 and scope connection member 304 are connected to the acoustic lens 309 by way of the connection bands 305 and 306 for smoothing out the steps of the respective connection parts with the both members of the balloon lock member 303 and scope connection member 304.

Such a configuration also hardly allows the balloon 360 to be caught by the connection part 305 or 306 when mounting the balloon 360 onto the ultrasonic transducer array 307 or removing the balloon 360 therefrom and therefore it is possible to perform the mounting or removal of the balloon 360 smoothly. It is also possible to prevent the acoustic lens 309 from peeling off the ultrasonic transducer array 307 or from being damaged when mounting or removing the balloon 360. Also enabled is an air bubble within the balloon 360 to be let out thereof smoothly. Also enabled is to protect the acoustic lens 309 from a foreign material, et cetera, when inserting the ultrasonic transducer array 307 into a human body.

The aforementioned embodiment may also be configured in a manner that, in either of the balloon lock member 303 or scope connection member 304, an outer diameter of the connection part with the acoustic lens 302 (or the acoustic lens 309) is larger than that of connection part for connecting the acoustic lens 302 (or the acoustic lens 309) to the balloon lock member 303 or scope connection member 304, and also the acoustic lens 302 (or the acoustic lens 309) is connected to the balloon lock member 303 or scope connection member 304 by way of the connection bands 305 and 306 for smoothing out the steps of the connection parts.

Meanwhile, the aforementioned embodiment is configured to connect the acoustic lens 302 (or the acoustic lens 309) to a scope part 355 by way of the scope connection member 304, it may, however, alternatively be configured to connect the acoustic lens 302 (or the acoustic lens 309) directly to the scope part 355. In such a case, an outer diameter of the scope connection part 355 at a part for connecting to the acoustic lens 302 (or the acoustic lens 309) is configured to be larger than that of the acoustic lens 302 (or the acoustic lens 309) at a part for connecting to the scope part 355, and also the acoustic lens 302 (or the acoustic lens 309) is connected to the scope part 355 by way of the connection band 306 for smoothing out the step at the connection parts.

As described above, the second embodiment of the present invention makes it possible to reduce a load applied to a connection part between the acoustic lens and endoscope structure member at the time of mounting a balloon onto the ultrasonic transducer array or removing the balloon therefrom.

Third Preferred Embodiment

Embodiment 1

A description of the present embodiment is on an electronic radial ultrasonic probe comprising a cylindrical array ultrasonic probe at the head of an insertion part which comprises an coaxial cable bundle connected to an transducer element group constituting an arrayed probe, a protective ground wire integrated with the coaxial cable bundle and a conductive body of approximately the same form of a conductor as an end face of the arrayed probe on the tip side, in which the protective ground wire is connected to the conductive body. The protective ground wire is one mutually shorting, nearby the ultrasonic probe, the shield wires of the coaxial cable group connected to each transducer element.

Figure 29:
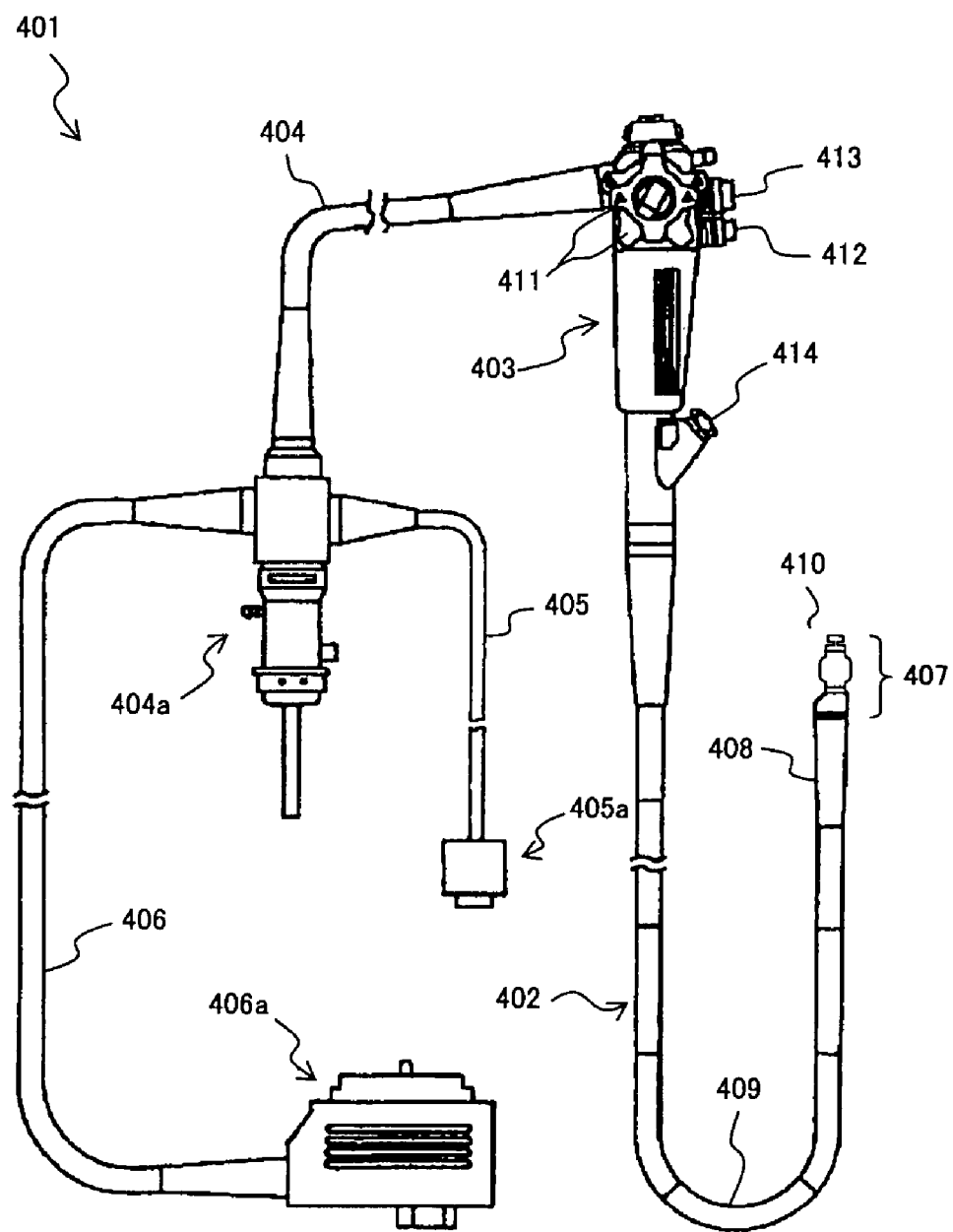
FIG. 29 is a diagram showing an external configuration of an ultrasonic endoscope according to the third preferred embodiment.

FIG. 29 shows an external configuration of an ultrasonic endoscope according to the third preferred embodiment (an embodiment 1 thereof). The ultrasonic endoscope 401 mainly comprises an insertion part 402 of a slender form inserted into an abdomen, an operation part 403 positioned at the base end of the insertion part 402 and a universal cord 404 extended from the side of the operation part 403.

The base end part of the universal cord 404 is equipped with an endoscope connector 404a for connecting to a light source apparatus (not shown herein). Extended from the endoscope connector 404a are an electric cable 405 detachably connected to a camera control unit (not shown herein) by way of an electric connector 405a, and an ultrasonic cable 406 detachably connected to an ultrasonic observation apparatus (not shown herein) by way of an ultrasonic connector 406a.

The insertion part 402 comprises by serially connecting, from the head, a hard head part 407 formed by a hard plastic member, a curve part 408 positioned behind the hard head part 407 and flexibly curved, and a flexible tube part 409, which is positioned behind the curve part 408, extended to the head part of the operation part 403, being a small diameter, long and flexible. And, the head of the hard head part 407 is equipped with an ultrasonic probe 410 arraying a plurality of piezoelectric elements for transceiving an ultrasonic wave.

The operation part 403 is equipped with an angle knob 411 for controlling the curve part 408 for curving in a desired direction, an air/water supplies button 412 for operating an air or water supply, a suction button 413 for performing a suction operation, a treatment instrument insertion entrance 414 functioning as entrance for a treatment instrument introducing into an abdomen, and et cetera.

FIG. 30 is an enlarged diagram of the hard head part 407 of the ultrasonic endoscope 401 shown in FIG. 29, with FIG. 30 (a) showing an external diagonal view diagram and FIG. 30 (b) showing an external comprisal diagram. The tip of the hard head part 407 is equipped with an ultrasonic probe 410 for enabling an electronic radial scan. The ultrasonic probe 410 is covered by a material forming an acoustic lens (i.e., an ultrasonic transception unit) 417.

Meanwhile, the hard head part 407 is featured with an incline part 407a. The incline part 407a is equipped with an illumination lens 418b constituting an illumination optical part for emitting an illumination light to an observation region, an object lens 418c constituting an observation optical part for grasping an optical image of the observation region, a suction-cum-forceps entrance 418d which is an opening for sucking an incised region or projecting a treatment instrument and an air/water supplies hole 418a which is an opening for supplying air and water.

A balloon is mounted onto the head of the ultrasonic endoscope for adjusting a contact state and a positional relationship with an internal abdominal wall, for which the head of the ultrasonic probe is featured with a balloon lock member 419 for locking the balloon.

Figure 31:
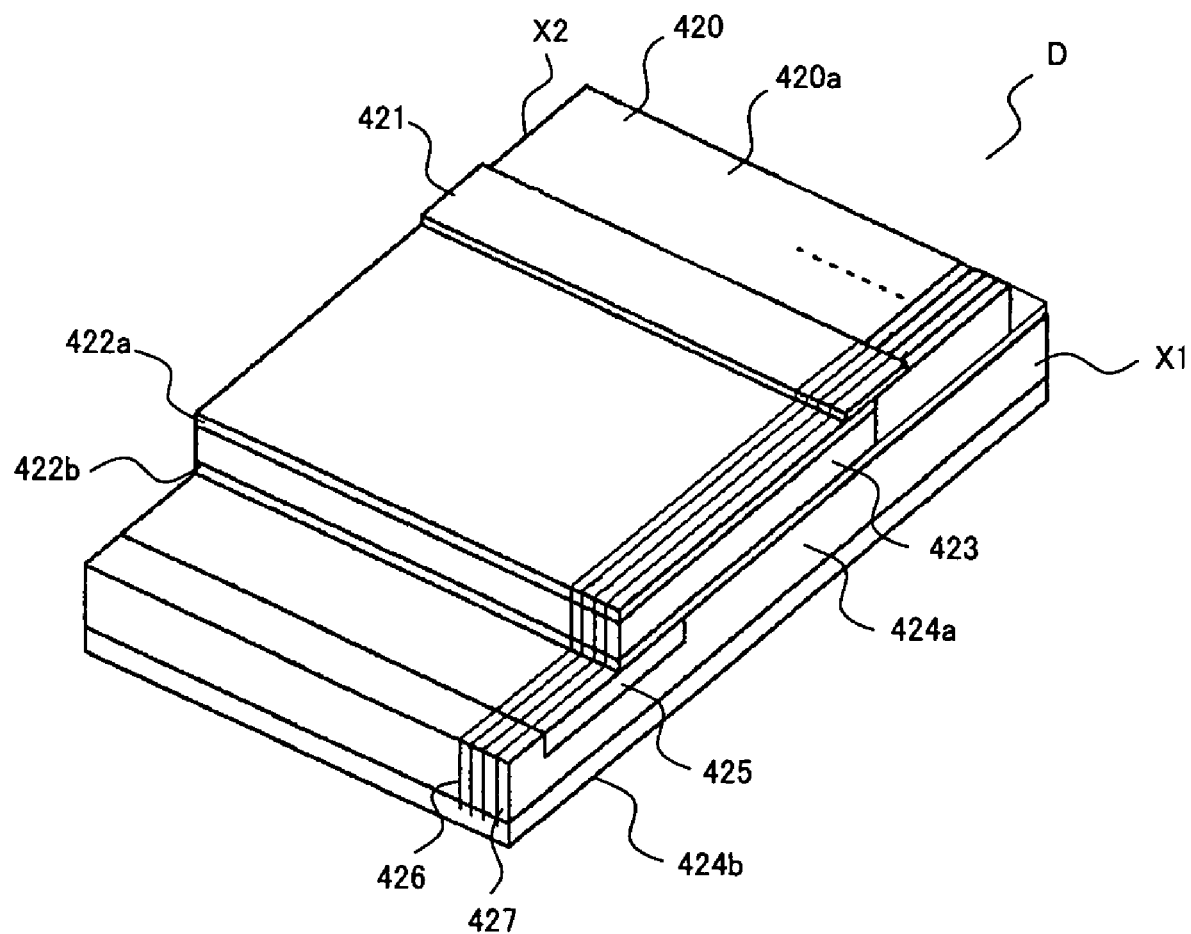
FIG. 31 is a diagram showing a production process (part 1) of an ultrasonic probe according to the third preferred embodiment (an embodiment 1 thereof)

FIG. 31 shows a production process (part 1) of an ultrasonic probe. Referring to FIG. 31, the first produced is a structure body D constituted by a substrate 420, a conductive body 421, electrodes 422 (i.e., 422a and 422b), a piezoelectric element 423, acoustic matching layers 424 (i.e., a first acoustic matching layer 424a and a second acoustic matching layer 424b), a conductive body 425 and a groove 426 when forming the ultrasonic probe 410. Now, a description is provided on a production of the structure body D.

The first is to form the second acoustic matching layer 424b followed by forming the first acoustic matching layer 424a. The next uses a dicing saw (i.e., a precision shearing machine) for forming a groove in the first acoustic matching layer 424a and pours a conductive resin 425 into the groove. The next forms a conductive layer 422b on the surface of the first acoustic matching layer 424a so as to unite with the conductive resin 425.

The next forms the piezoelectric element 423 on the conductive layer 422b and forms the conductive layer 422a thereon. The conductive layers 422a and 422b constitute the electrodes 422a and 422b for applying a voltage to the piezoelectric element 423. The next mounts the substrate 420 on the side of the piezoelectric element 423 and also on the conductive layer 422b. The surface of the substrate 420 is featured with an electrode layer 420a. The next mounts the conductive body 421 for electrically connecting the electrode 420a to the electrode 422a.

The next forms a plurality of grooves of the width of tens micrometers (i.e., diced grooves) 426 by cutting in the formed structure body D as described above. The width of the groove is preferably 20 to 50 micrometers. In this event, the cut-in of the structure body D is such as to leave tens micrometers of the second acoustic matching layer 424b uncut in lieu of the layer being completely cut. Approximately 200 pieces of such grooves 426 are formed. Here, the divided each of the transducers is called an transducer element 427.

Note that the present embodiment as described above is of a two-layer matching, and therefore a material for the first acoustic matching layer 424a preferably uses an epoxy resin containing a filler such as alumina and titania ($TiO_2$), et cetera, which that of the second acoustic matching layer 424b preferably uses an epoxy resin not containing a filler. In the case of a three-layer matching, a material for the first acoustic matching layer preferably uses a carbon or epoxy resin containing a machinable ceramics, a filler or fibers, that of the second acoustic matching layer preferably uses an epoxy resin containing a very little amount (i.e., a lower rate of content as compared to the case of two-layer matching) of filler such as alumina, titania, et cetera, and that of the third acoustic matching layer preferably uses an epoxy resin not containing a filler.

The piezoelectric element 423 may use one invested with electrodes on both of the principal surfaces in advance. And the electrode layer 422a may utilize an electrode invested to the piezoelectric element in advance.

The next curves the structure body D to a cylindrical form so as to make the side faces X1 and X2 of the layered body facing each other as shown in FIG. 32 (a).

The next forms the acoustic lens 417 on the cylindrical surface (named as "structure body E" hereinafter) as shown in FIG. 32 (b). The acoustic lens 417 may use a pre-produced single body of acoustic lens for combining with the structure body D which is formed as a cylindrical shape, or insert a cylindrically formed structure body D into a mold and pour the acoustic lens material into the mold, thereby forming an acoustic lens 417. Note that a lens part 417a of the acoustic lens 417 is the part functioning as acoustic lens.

The next mounts a circular structure member 430a internally from the opening part of the structure body E as shown in FIG. 32 (c). In this event, the structure member 430a is mounted so as to position itself on the substrate 420 (refer to FIG. 33 (a)). A structure member 430b is likewise mounted onto the opening part on the other side. In this event, the structure member 430b is mounted so as to position itself on the conductive material 425 (refer to FIG. 33 (a)). The outer surface of the structure member 430b is covered with a metal such as a copper foil, et cetera.

Figure 33:
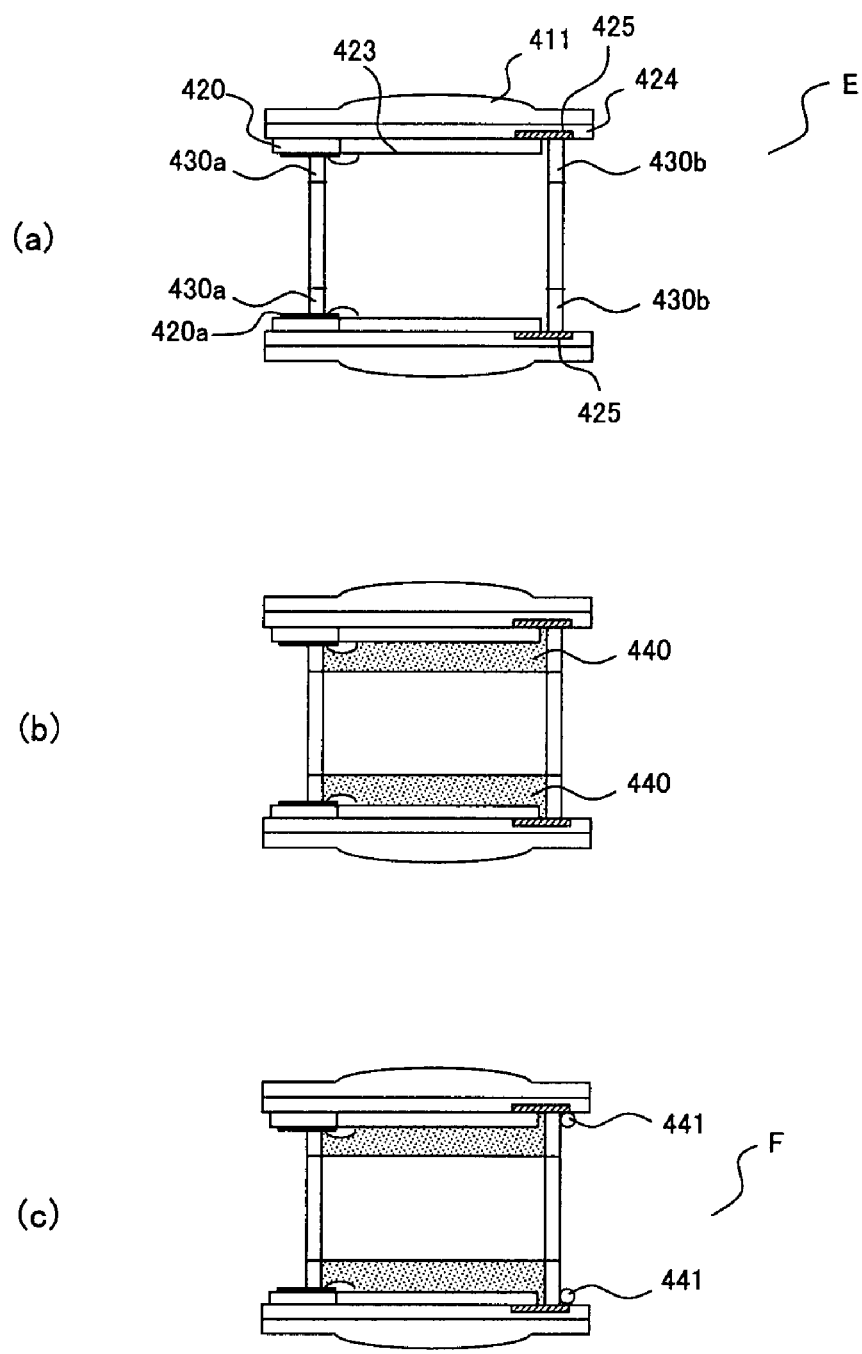
FIG. 33 is a diagram showing a production process (part 3) of an ultrasonic probe according to the third preferred embodiment (an embodiment 1 thereof)

FIG. 33 shows a cross-section of the structure body E mounting the structure members 430. Mounting the structure members 430 (i.e., 430a and 430b) as shown in FIG. 32 (c), followed by (refer to FIG. 33 (a)), filling in between the structure members 430a and 430b with a backing material 440 (refer to FIG. 33 (b)). A gelatinous epoxy resin mixed with alumina filler is used for the backing material 440. The next connects the conductive material 425 to a conductive face of the structure member 430b electrically by means of a conductive material 441 (refer to FIG. 33 (c)) (the structure body produced in FIG. 33 is named as "structure body F" hereinafter).

The next inserts a cylindrical structure member 450 from one side of the opening part of the structure body F (i.e., a side equipped with the substrate 420) as shown in FIG. 34 (a). The cylindrical structure member 450 is constituted by a cylindrical part 453 and a circular flange 452 equipped on one end thereof. The surface of the flange 452 is equipped with a printed wiring plate 454 of which the surface is featured with an electrode pad 451 of tens to hundreds in number. Furthermore, a cable bundle 462 is internally led though the cylindrical structure member 450 with the tip of which being soldered with each pad 451 (i.e., the cable 462 is connected by soldering in the inside (i.e., toward the center of circle)) of the electrode pad 451). Note that the cable 462 usually uses a coaxial cable for a noise reduction.

The cylindrical structure member 450 is made of an insulator material (e.g., the engineering plastics). The insulator material includes polysulfone, polyether imide, polyphenylene oxide, epoxy resin, et cetera, for example. The surface of the cylindrical part 453 is plated with a conductive body (i.e., a metal film 463). Note that the surface of the cylindrical part 453 is featured with a hole 455, and a ground wire 471 extended from the cable bundle 462 led through the cylindrical structure member 450 comes out of the hole 455 and is connected to the metal film 463 which is plated on the outer side surface of the cylindrical part 453.

When inserting the cylindrical member 450 thus connected to the cable 462 into the structure body F, the flange 452 part of the cylindrical member 450 hits the structure members 430 of the structure body F, fixing the position of the cylindrical structure member 450, thus positioning it in the inside of the ultrasonic probe 410.

FIG. 34 (b) shows the situation of connecting the electrode 420a of the transducer element 427 to the outer side of the electrode pad 451 (i.e., the electrode pad part in the outer circumference of the circle) by using a wire 490 after the cylindrical structure member 450 is inserted and positioned (the structure body produced as shown in FIG. 34 (b) is named as "structure body G" hereinafter).

Incidentally, the balloon lock member 419 is mounted onto the opening part of an ultrasonic probe for locking an edge of a balloon. A support member is required to retain the balloon lock member 419 at the opening part of the ultrasonic probe. The next is a description of the balloon lock member 419 by referring to FIG. 35.

Figure 35:
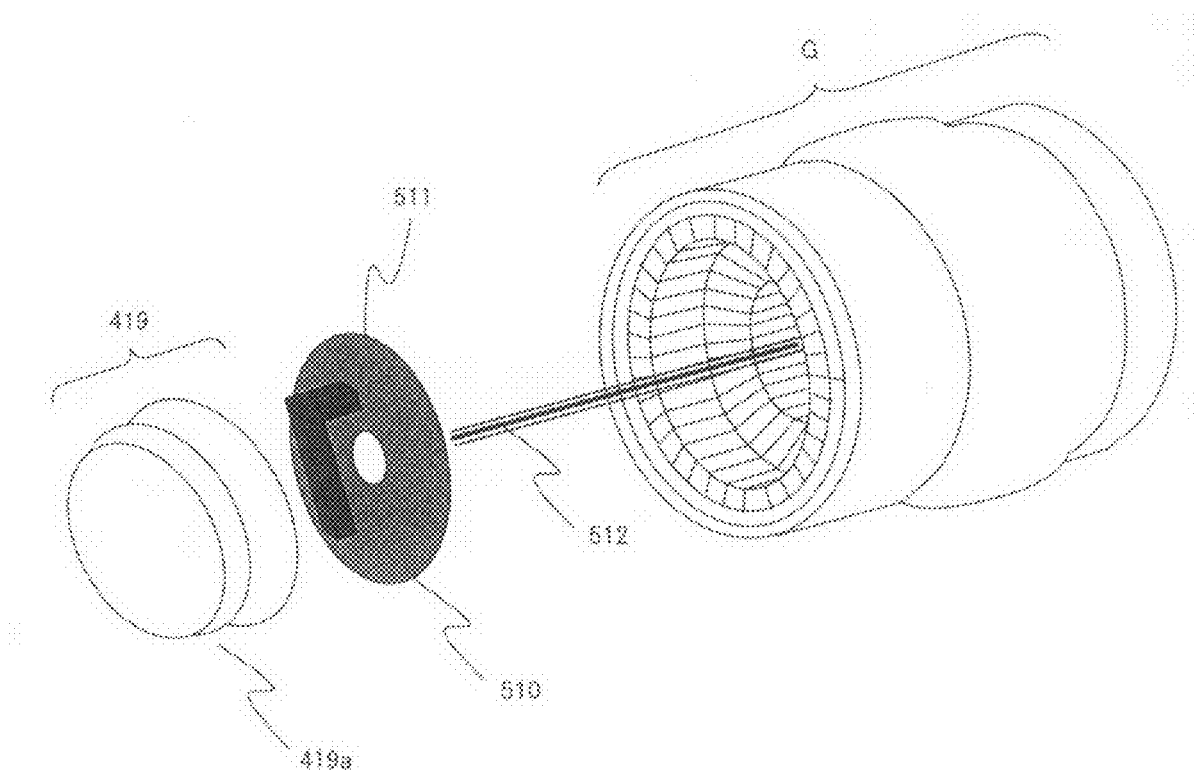
FIG. 35 exemplifies a balloon lock member and its support member which are mounted onto a structure body G according to the third preferred embodiment (an embodiment 1 thereof)

FIG. 35 exemplifies the balloon lock member 419 and the support member which are mounted onto the structure body G. A flat surface of a circular conductive plate 510 with a hole at the center is equipped with a support member 511 which is featured as an approximate alphabet L, that is, with one overhang at the end. The conductive plate 510 is electrically and mechanically connected to a protective ground wire 512 which is extended from the opening part of the structure body G. The conductive plate 510 is then mounted to the opening part of the structure body G.

The balloon lock member 419 is featured with a cavity in which the support member 511 is inserted, is equipped with a balloon lock groove 419a for locking a balloon, and is mounted so as to cover the opening part of the structure body G.

Figure 36:
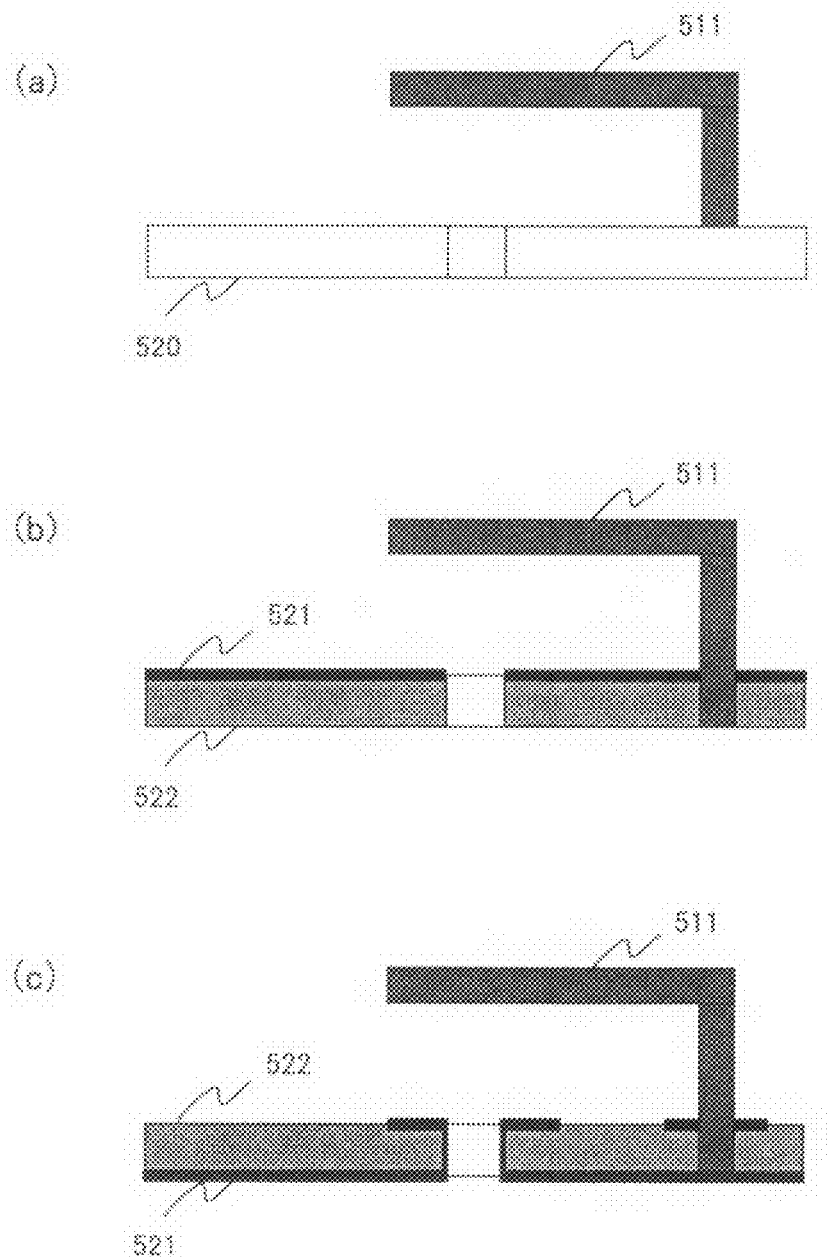
FIG. 36 exemplifies a variation of a conductive plate 510 according to the third preferred embodiment (an embodiment 1 thereof)

FIG. 36 exemplifies a variation of the conductive plate 510. FIG. 36 (a) exemplifies one using a metal plate 520 as a conductive plate 510. The support member 511 is fixed onto the metal plate 520 by means of a soldering or adhesion.

FIG. 36 (b) shows an example using, as a conductive plate 510, a plastic plate 522 (i.e., a printed circuit material) with one surface being covered with a copper foil 521. The support member 511 is fixed onto the plastic plate 522, on the surface of which is covered with the copper foil 521 by means of a soldering or adhesion.

FIG. 36 (c) shows an example using, as a conductive plate 510, a plastic plate (i.e., a printed circuit material) equipped with a through-hole (i.e., a hole featured with a copper foil on the hole surface for electrically connecting the two surfaces). The support member 511 is fixed on the face on the side featured with an electrode pattern. In this case, a thermal capacity of the soldered part is small as to make the soldering easy and hence improve reliability.

Figure 37:
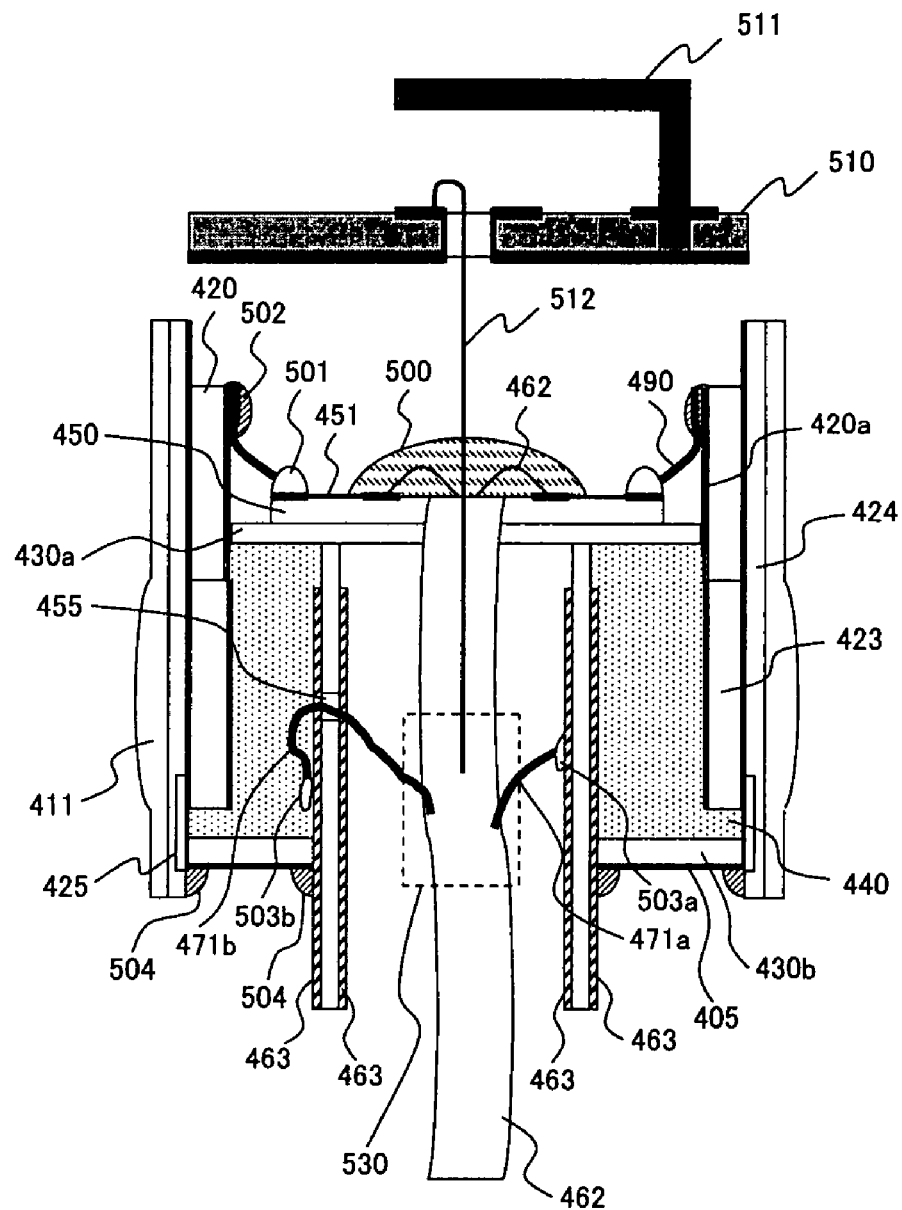
FIG. 37 shows a cross-sectional diagram when mounting a conductive plate 510 onto a structure body G according to the third preferred embodiment (an embodiment 1 thereof)

FIG. 37 shows a cross-sectional diagram when mounting the conductive plate 510. As described above, the cable 462 is connected to the side of the center direction of the flange of the electrode pad 451 by a soldering. One end of a wire 490 is connected to the side of the center direction of the flange of the electrode pad 451 by a soldering 501, while the other end is connected to the signal-side electrode 420a existing on the substrate 420 of the transducer element by a soldering 502. Note that the aforementioned connection is carried out by using a short wire 490 for preventing a shorting by the wire contacting the adjacent signal-side electrode 420a. Then, the entirety of the connection part between the cable 462 and electrode pad 451 is covered with a potting resin 500 in order to prevent the cable 462 from coming off the electrode pad 451 as a result of the cable 462 being pulled by a load applied thereto.

A copper foil 505 is filmed on a surface of the structure member 430b, and further the surface of the structure members 430 is connected to the cylindrical surface of the acoustic matching layers 424 and cylindrical member 450 by a conductive resin (e.g., a solder) 504.

Note that the ground wires 471 (i.e., 471a and 471b) are extended from the cable bundle 462 and connected to the metal film 463 by soldering 503a and 503b, respectively, as described for FIG. 34 (a).

FIG. 38 is an enlarged diagram of the coaxial cable group 462 enclosed by the dotted line frame 530 indicated in FIG. 37. FIG. 38 (a) is the enlarged diagram viewed from a side, while FIG. 38 (b) is a cross-sectional diagram, viewed from above, of one coaxial cable 540 among the coaxial cable group 462. Note that a bundle of individual coaxial cables 540 is named as the coaxial cable group 462 in the following description.

Each coaxial cable 540 has a signal wire 541 which is covered with a dielectric body 542, around of which is covered with a shield wire (i.e., a signal ground wire) 543 and further covered with an outer coat 544. The signal wire 541 is electrically connected to the corresponding piezoelectric element.

Referring to FIG. 38, the outer coat of each coaxial cable 540 is removed until a predetermined position. And the shield wires 543 of the coaxial cables 540 are mutually shorted. Ground wires 545 are extended from the shorted shield wire parts.

The ground wires 545 are connected to the conductive plate 510 as the protective ground wire 512, and are connected to the metal film 463 by the soldering 503a and 503b as the ground wires 471 (i.e., 471a and 471b), respectively, as shown in FIG. 37. The coaxial cable 462 is connected to an ultrasonic observation apparatus (not shown herein) after being led through the inside of an insertion part 2 of the ultrasonic endoscope 401, and the shield wires 543 of the coaxial cable group 462 are also connected to the ground (GND) of the aforementioned ultrasonic observation apparatus.

Figure 39:
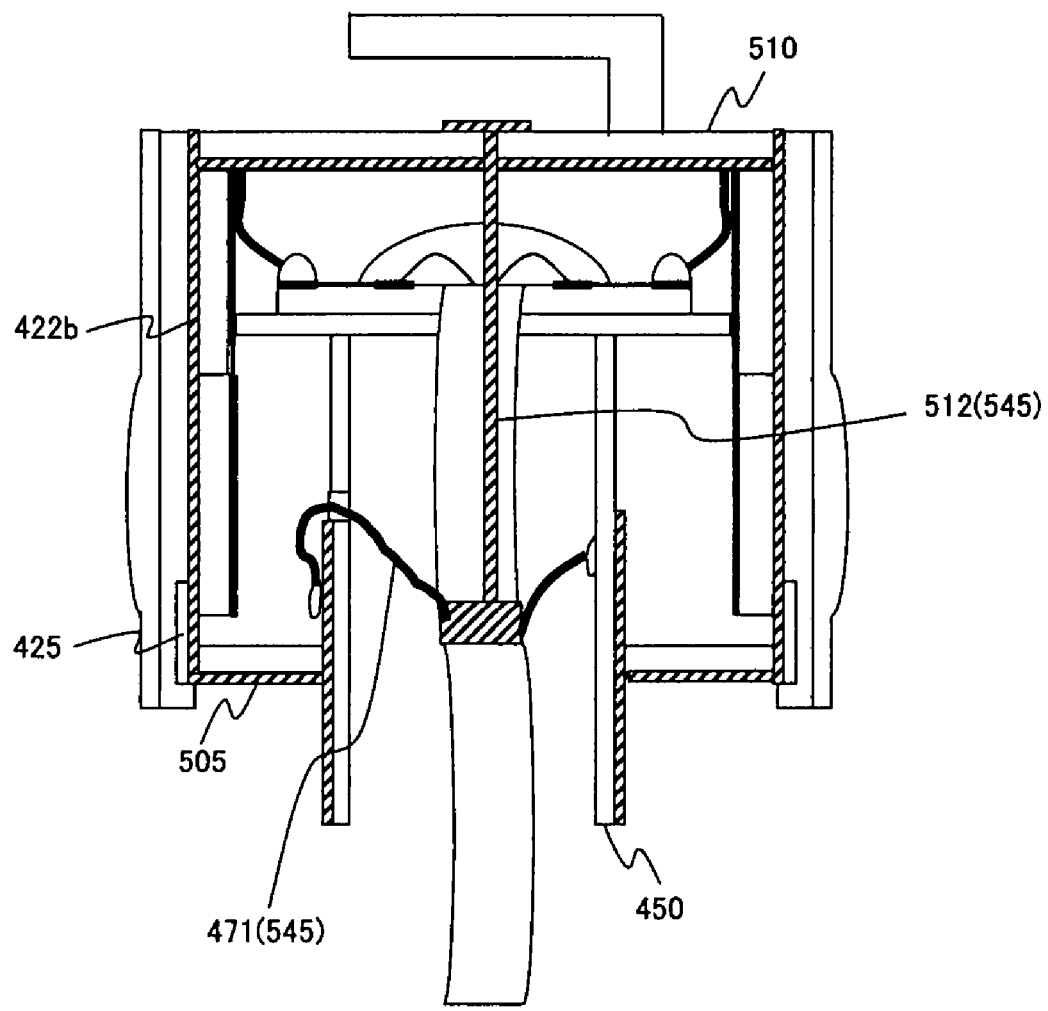
FIG. 39 shows a cross-sectional diagram of a state of protective-grounding an ultrasonic probe 530 according to the third preferred embodiment (an embodiment 1 thereof)

FIG. 39 shows a cross-sectional diagram of a state of protectively grounding the ultrasonic probe 410 according to the present embodiment. FIG. 39 shows an emphasis of parts with a protective grounding (i.e., diagonally hatched parts 570) by attaching the conductive plate 510 to the structure body G in the configuration shown in FIG. 37. Note that a part of FIG. 37 is omitted for convenience of the description.

Referring to FIG. 39, the entire frame of the ultrasonic probe is protectively grounded by the ground wires 512 and 471, the bottom surface of the conductive body 510, the electrode 422b, the copper foil 505 featured on the bottom surface the structure member 430b. Therefore, even if the ultrasonic probe is mechanically damaged, resulting in exposing the interior, such a part is protectively grounded.

The present embodiment is configured to share the protective grounding and signal ground (GND), thereby reducing the number of components, hence contributing to a miniaturization of the ultrasonic probe.

As described thus far, the entirety of the ultrasonic probe can be covered with a protective grounding. Therefore, even if the head part of an ultrasonic endoscope is mechanically damaged, the electric shock can be prevented since the parts exposing externally to the ultrasonic probe are protectively grounded.

Embodiment 2

A description for the present embodiment is on an electronic radial ultrasonic probe separating a protective grounding and a signal grounding (GND), while the embodiment 1 shares the protective grounding and signal GND.

FIG. 40 is a diagram showing a part of a production process of an ultrasonic probe according to the third preferred embodiment (an embodiment 2 thereof). FIG. 40 (a) is a diagram corresponding to FIG. 31. Different from the configuration of FIG. 31, one shown in FIG. 40 comprises a conductive layer 422b being featured in a part connecting to a piezoelectric element, and it is not featured in between a substrate 420 and a first acoustic matching layer 424a.

The present embodiment is also configured that a structure body D shown in FIG. 40 (*a*) is produced first, followed by featuring a metal film on the surface of the structure body D and featuring an acoustic lens 417.

Also, metal films are featured on both surfaces of the structure member 430b mounted as shown in FIG. 33 (*a*). Meanwhile, a cylindrical structure member 450 used for the present embodiment is intermittently plated with a metal films 546 (i.e., 546a and 546b) as shown in FIG. 40 (*b*). The metal film 546a is not electrically connected to the metal film 546b. From a hole 547a opening on the side surface 453 of the cylindrical structure member 450 comes out the above noted signal GND line 565 and is connected to the metal film 546a. And from a hole 547b comes out a protective ground wire 560 which is then connected to the metal film 546b. Except for the process described above, the production process is the same as that of the embodiment 1.

Figure 41:
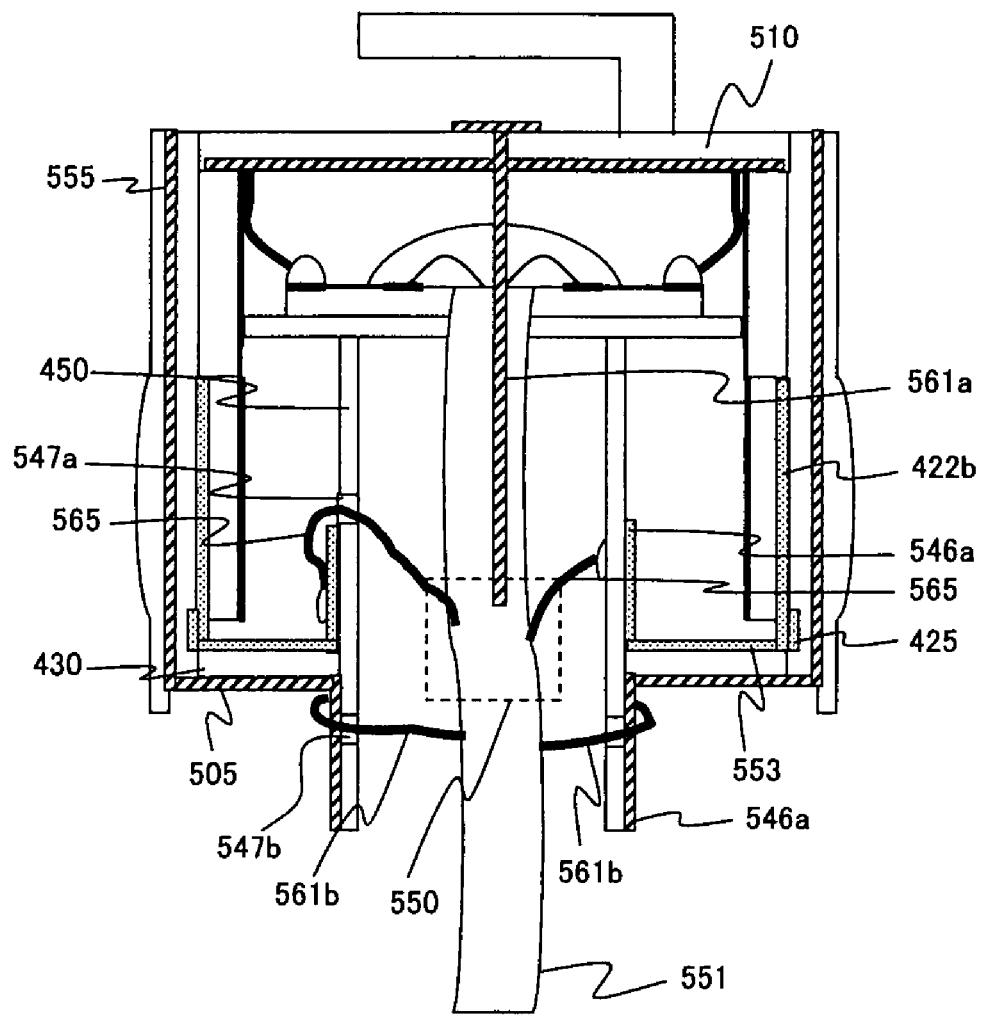
FIG. 41 shows a cross-section of an ultrasonic probe 10 separating between a protective grounding and a signal ground according to the third preferred embodiment (an embodiment 2 thereof)

FIG. 41 shows a cross-section of an ultrasonic probe 410 separating between a protective grounding and a signal ground according to the third preferred embodiment (an embodiment 2 thereof). FIG. 41 shows the emphases of a protectively grounded part (i.e., diagonally hatched part 580) and a part (i.e., shaded part 581) equipped with a signal GND, by mounting a structure body G in the configuration of FIG. 37.

From a coaxial cable group 551 extends a signal GND wire 565 which is then soldered to a metal film 546a featured on the surface of a cylindrical structure member 450. From the coaxial cable group 551 extend protective ground wires 561 (i.e., 561a and 561b). Of them, the protective ground wire 561a is soldered to a conductive body 510. The protective ground wire 561b is soldered to a metal film 546b featured on the surface of the cylindrical structure member 450. And a conductive resin 425 is electrically connected to a metal film 553 featured on the surface of a structure member 430 on the internal side of the ultrasonic probe. Note that a part is also omitted for convenience of the description as in the case of FIG. 39.

FIG. 42 shows an enlarged diagram of a part of a coaxial cable group 551 which is enclosed by a dotted line frame 550. FIG. 42 (*a*) is an enlarged diagram viewed from the side direction, while FIG. 42 (*b*) is a cross-sectional diagram of a coaxial cable group 551 viewed from above. Note that a bundle of individual coaxial cables 540 is named as the coaxial cable group 551 in the following description.

A comprisal of each coaxial cable 540 is the same as one shown in FIG. 37. And individual shield wires (i.e., signal GND wires) 543 of the coaxial cable 540 are mutually shorted. From the shorted shield wire part extend ground wires (i.e., signal GND wires) 565.

A plurality of coaxial cables 540 is bundled together and covered with an integrated shield wire 560 which is further covered with an outer coat 562. From the integrated shield wire 560 extend the ground wires (i.e., protective grounding wires) 561.

Referring to FIG. 41, the entire frame of the ultrasonic probe is protectively grounded by the protective ground wires 561a and 561b, the bottom surface of the conductive body 510, the metal film 555 featured on the outer surface of the acoustic matching layer, the copper foil 505 featured on the bottom surface of the structure member 430b and the metal film 546b featured on the side surface of the cylindrical structure member 450.

The protective grounding is separated from the signal GND constituted by the signal GND wire 565, the electrode 422b, the copper foil 553 featured on the top surface of the structure member 430b and the metal film 546a featured on the side surface of the cylindrical structure member 450. That is, the protective ground wire (i.e., the integrated shield wire 560) is electrically independent of the shield of the coaxial cable group (i.e., the signal GND wires 565) connected to the individual transducer elements.

Thus covering the entirety of the ultrasonic probe with a protective grounding and equipping the interior with a signal GND make it possible to shut off an external electrical noise by the protective grounding, hence enabling a suppression of an influence of the electrical noise to the signal GND (i.e., improving an anti-noise property). This makes it possible to suppress a fluctuation as a reference voltage to a signal line by minimizing a variation of potential of the signal GND, thereby making it possible to obtain an ultrasonic image signal with a smaller noise component.

As described above, even if the tip part of the ultrasonic endoscope is mechanically damaged, an electric shock can be prevented. And the separation of the protective grounding from the signal GND enables a further improvement of an anti-noise property as compared to the embodiment 1.

As such, the third embodiment of the present invention makes it possible to prevent an electric shock even if a mechanical damage is caused to the insulator member at the tip of the an ultrasonic endoscope because of the structure externally exposing the protective grounding part.

Note that the first through third embodiment use an electronic radial ultrasonic probe utilizing a piezoelectric element, the present invention, however, is applicable to an electronic radial ultrasonic probe utilizing a capacitive transducer (i.e., c-MUT).

The invention claimed is:

1. An electronic radial ultrasonic probe comprising an electronic radial array which comprises a plurality of ultrasonic transducers being continuously arrayed circularly around an insertion axis as center and also for which a transmission/reception of an ultrasonic wave is controlled by electronically selecting the plurality of ultrasonic transducer, comprising:

a support member equipped on the electronic radial array;

a lock member featured with a cavity in which the support member is inserted and with a lock groove for locking a balloon which is mounted in a manner to cover the electronic radial array and in which an ultrasonic medium is filled; and a filler member constituted by an adhesive material converting from a fluid state to a solid state, and is filled in the cavity.

2. The electronic radial ultrasonic probe according to claim 1, wherein said support member is formed in a manner that the support member is caught by said filler member in said solid state when the filler member is converted into the solid state after the support member is inserted into the filler member which is filled within said cavity in said fluid state, and the cavity is formed in a manner that the filler member in the solid state catches said lock member when the filler member in the fluid state within the cavity is converted into a solid state.

3. The electronic radial ultrasonic probe according to claim 1, wherein said support member is equipped on said electronic radial array, and formed in a manner that two certain cross-sectional area sizes and/or forms in the direction perpendicular to said insertion axis are mutually different;

the support member is inserted into said lock member which is equipped with a cavity being formed in a manner that two certain cross-sectional area sizes and/or forms in the direction perpendicular to the insertion axis are mutually different, and with a lock groove for locking a balloon which is mounted in a manner to cover the electronic radial array and in which an ultrasonic medium is filled; and said filler member is constituted by an adhesive material converting from a fluid state to a solid state, and adheres said support member to said lock member and also combines the support member and lock member together in a manner to catch each other by converting to a solid state from a fluid state when filling the cavity.

4. The electronic radial ultrasonic probe according to claim 1, wherein said support member is formed in a manner that a cross-sectional area size in the direction perpendicular to said insertion axis on the tip side of the support member is larger than on the root side thereof.

5. The electronic radial ultrasonic probe according to claim 1, wherein said cavity is formed in a manner that a cross-sectional area size in the direction perpendicular to said insertion axis is larger on the bottom side of the cavity than on the opening side thereof.

6. The electronic radial ultrasonic probe according to claim 1, wherein said support member is formed so as to have one or more overhangs.

7. The electronic radial ultrasonic probe according to claim 1, wherein said cavity is formed so as to have one or more overhangs in an internal side surface.

8. The electronic radial ultrasonic probe according to claim 1, wherein said support member is featured with a screw on a side surface.

9. The electronic radial ultrasonic probe according to claim 1, wherein said cavity is featured with a screw on an internal side surface.

10. The electronic radial ultrasonic probe according to claim 1, wherein said support member is equipped on said electronic radial array and is featured with a screw on a side surface, and said lock member is equipped with a cavity which is featured with a screw in an internal side surface corresponding to the support member, and a lock groove for locking a balloon which is mounted in a manner to cover the electronic radial array and in which an ultrasonic medium is filled.

11. The electronic radial ultrasonic probe according to claim 1, wherein said support member is formed by a material through which an x-ray is difficult to transmits.

12. The electronic radial ultrasonic probe according to claim 1, wherein said support member is formed by a material containing a magnetic body.

13. The electronic radial ultrasonic probe according to claim 1, wherein said support member is wound by a coil.

14. The electronic radial ultrasonic probe according to claim 13, wherein said coil is connected to coil signal line going through a cable constituted by collecting signal wires for electronically selecting said plurality of ultrasonic transducers.

15. The electronic radial ultrasonic probe according to claim 1, wherein said support member is constituted by an adhesive material converting from a fluid state to a solid state, and said cavity is formed in a manner that the support member and adhesive material in the solid state are caught with said lock member when the adhesive material is converted into the solid state after the support member is inserted into the adhesive material which is filled within the cavity in the fluid state.

16. The electronic radial ultrasonic probe according to claim 1, wherein said support member is fixed by a rope-like member going through a cable constituted by collecting signal wires for electronically selecting said plurality of ultrasonic transducers.

17. An ultrasonic endoscope apparatus comprising an electronic radial ultrasonic probe noted in claim 1.

* * * * *